US007419670B2

(12) United States Patent
Zhong et al.

(10) Patent No.: US 7,419,670 B2
(45) Date of Patent: Sep. 2, 2008

(54) METHOD OF TREATING ARTHRITIS WITH SERP-1 AND AN IMMUNOSUPPRESSANT

(75) Inventors: Robert Z. Zhong, London (CA); Alexandra Lucas, London (CA); Grant D. McFadden, London (CA)

(73) Assignee: Viron Therapeutics, Inc., London, Ontario (CA)

( * ) Notice: Subject to any disclaimer, the term of this patent is extended or adjusted under 35 U.S.C. 154(b) by 100 days.

(21) Appl. No.: 10/381,875

(22) PCT Filed: Sep. 28, 2001

(86) PCT No.: PCT/CA01/01369

§ 371 (c)(1),
(2), (4) Date: Aug. 19, 2003

(87) PCT Pub. No.: WO02/26245

PCT Pub. Date: Apr. 4, 2002

(65) Prior Publication Data

US 2004/0029801 A1 Feb. 12, 2004

Related U.S. Application Data

(60) Provisional application No. 60/236,939, filed on Sep. 29, 2000.

(51) Int. Cl.
*A61K 39/00* (2006.01)
(52) U.S. Cl. .................................................. 424/185.1
(58) Field of Classification Search ....................... None
See application file for complete search history.

(56) References Cited

U.S. PATENT DOCUMENTS

| 5,686,409 | A | 11/1997 | McFadden et al. |
| 5,688,824 | A | 11/1997 | Williams |
| 5,917,014 | A | 6/1999 | McFaddenm et al. |
| 5,939,525 | A * | 8/1999 | McFadden et al. .......... 530/324 |
| 7,285,530 | B2 | 10/2007 | Lucas et al. |
| 2003/0171263 | A1 | 9/2003 | Lucas et al. |

FOREIGN PATENT DOCUMENTS

| EP | 0356945 B1 | 11/1993 |
| EP | 0567816 A1 | 11/1993 |
| EP | 0985412 A2 | 3/2000 |
| EP | 1365798 A0 | 4/2002 |
| EP | 0817646 B1 | 1/2003 |
| EP | 1223971 B1 | 6/2005 |
| JP | H2-108633 | 4/1990 |
| JP | H6-9425 | 1/1994 |
| WO | WO 91/15221 | 10/1991 |
| WO | WO 92/06706 | 4/1992 |
| WO | WO 92/22320 | 12/1992 |
| WO | WO 93/10812 | 6/1993 |
| WO | WO 95/27503 | 10/1995 |
| WO | WO 96/030042 | 10/1996 |
| WO | WO 97/10006 | 3/1997 |
| WO | WO 9962540 | * 12/1999 |
| WO | WO 00/45834 | 8/2000 |
| WO | WO 00/53793 | 9/2000 |
| WO | WO 01/30379 | * 3/2001 |
| WO | WO 01/30379 A2 | 5/2001 |
| WO | WO 01/38790 | 5/2001 |
| WO | WO 01/039790 | 6/2001 |
| WO | WO 02/026245 | 4/2002 |
| WO | WO 2004/039391 | 5/2004 |

OTHER PUBLICATIONS

Mikayama et al. PNAS, 1993. 90: 10056-10060.*
Burgess et al ., J Cell Biol. 111:2129-2138, 1990.*
Whisstock et al ., Quarterly Review of Biophysics, 2003, 36, pp. 307-340.*
Mc Cune et al Curr.Opin Rheumatol, 1993, vol. 3, pp. 282-292.*
Strom et al. Therapeutic Immunology, Austen et al. (Ed.) Blackwell Science, Cambridge MA, 1996.*
Bernard Hausen, et al., "Viral Serine Proteinase Inhibitor (Serp-1) Effectively Decreases the Incidence of Graft Vasculopathy in Heterotopic Hear Allografts", Transplantation, vol. 72, pp. 364-368 (2001).
Alexandra Lucas, et al., "Transplant Vasculopathy: Viral Anti-Inflammatory Serpin Regulation of Atherogenesis", The Journal of Heart and Lung Transplantation, vol. 19, pp. 1029-1038 (2000).
Abstract of Bernard Hausen, et al., "Viral Serine Proteinase Inhibitor (Serp-1) Effectively Decrease the Incidence of Graft Vasculopathy in Heterotopic Hear Allografts", Transplantation, vol. 72, pp. 364-368 (2001).
Abstract of Alexandra Lucas, et al., "Transplant Vasculopathy: Viral Anti-Inflammatory Serpin Regulation of Atherogenesis", The Journal of Heart and Lung Transplantation, vol. 19, pp. 1029-1038 (2000).
Aziz et al., "Transplant Arterial Vasculopathy: Evidence for a Dual Pattern of Endothelial Injury and the Source of Smooth Muscle Cells in Lesions of Intimal Hyperplasia," *J. Heart Lung Transplant.* 14:S123-S136, 1995.
Abraham et al., "$\alpha_4$-Integrins Mediate Antigen-Induced Late Bronchial Responses and Prolonged Airway Hyperresponsiveness in Sheep," *J. Clin. Invest.* 93:776-787, 1994.
Abraham et al., "Characterization of a Late Phase Pulmonary Response after Antigen Challenge in Allergic Sheep," *Am. Rev. Respir. Dis.* 128:839-844, 1993.

(Continued)

*Primary Examiner*—Michail A Belyavskyi
(74) *Attorney, Agent, or Firm*—Clark & Elbing LLP; Kristina Bieker-Brady

(57) ABSTRACT

Compositions and methods for treating inflammatory cell infiltration in a tissue of a mammalian subject are provided. The method involves administering a therapeutically effective amount of SERP-1/immunosuppressant combination admixed with a pharmaceutically acceptable carrier to a subject in need of such treatment. The compositions and methods of the present invention are useful for treating numerous inflammatory based diseases and injuries.

10 Claims, 3 Drawing Sheets

OTHER PUBLICATIONS

Figure 1:
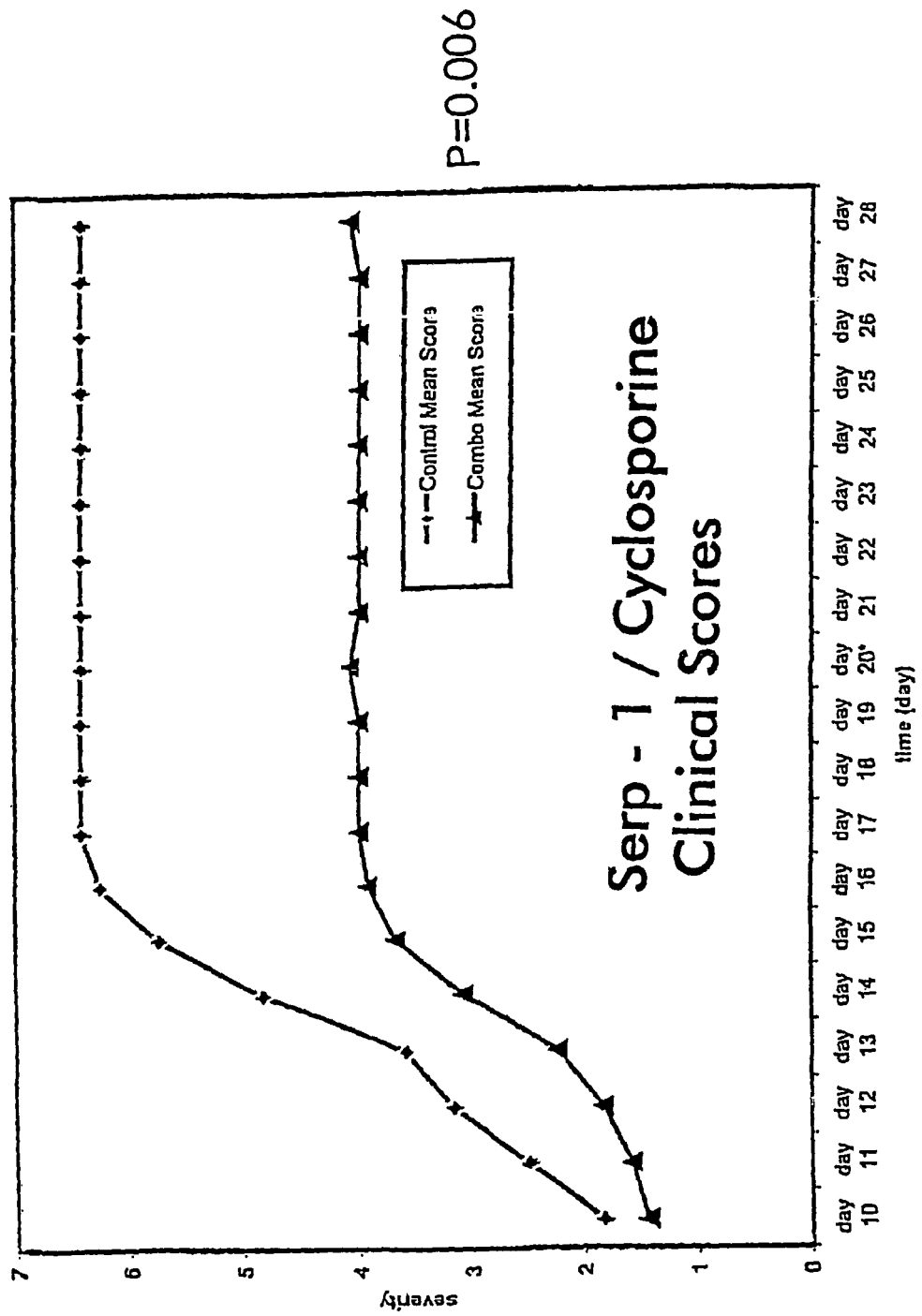

Barsoum, "Introduction of Stable High-Copy-Number DNA into Chinese Hamster Ovary Cells by Electroporation," *DNA Cell. Biol.* 9:293-300, 1990.

Bédard et al., "Prevention of Chronic Renal Allograft Rejection by SERP-1 Protein," *Transplantation* 81:908-914, 2006.

Ben-Nun et al., "The Rapid Isolation of Clonable Antigen-Specific T Lymphocyte Lines Capable of Mediating Autoimmune Encephalomyelitis," *Eur. J. Immunol.* 11:195-199, 1981.

Bowes et al., "Diaspirin Cross-Linked Hemoglobin Improves Neurological Outcome Following Reversible but not Irreversible CNS Ischemia in Rabbits," *Stroke* 25:2253-2257, 1994.

Burkly et al., "Protection Against Adoptive Transfer of Autoimmune Diabetes Mediated Through Very Late Antigen-4 Integrin," *Diabetes* 43:529-534, 1994.

Colvin, "CADI, Canti, Cavi," *Transplantation* 83:677-678, 2007.

Cosimi et al., "In Vivo Effects of Monoclonal Antibody to ICAM-1 (CD54) in Nonhuman Primates with Renal Allografts," *J. Immunol.* 144:4604-4612, 1990.

Dai et al., "Serp-1, a Viral Anti-Inflammatory Serpin, Regulates Cellular Serine Proteinase and Serpin Responses to Vascular Injury," *J. Biol. Chem.* 278:18563-18572, 2003.

Davis et al., "The Effect of Age on Cerebral Oedema, Cerebral Infarction and Neuroprotective Potential in Experimental Occlusive Stroke," *Acta Neurochir. Suppl.* 60:282-284, 1994.

Davison and Moss, "New Vaccinia Virus Recombination Plasmids Incorporating a Synthetic Late Promoter for High Level Expression of Foreign Proteins," *Nucl. Acids Res.* 18:4285-4286, 1990.

Doerschuk et al., "CD18-Dependent and -Independent Mechanisms of Neutrophil Emigration in the Pulmonary and Systemic Microcirculation of Rabbits," *J. Immunol.* 144:2327-2333, 1990.

Fava et al., "Transforming Growth Factor β1 (TGF-β1) Induced Neutrophil Recruitment to Synovial Tissues: Implications for TGF-β-Driven Synovial Inflammation and Hyperplasia," *J. Exp. Med.* 173:1121-1132, 1991.

Friedrichs et al., "Effects of Heparin and N-Acetyl Heparin on Ischemia/Reperfusion-Induced Alterations in Myocardial Function in the Rabbit Isolated Heart," *Circulation Res.* 75:701-710, 1994.

Fritz, "Proteinase Inhibitors in Severe Inflammatory Processes (Septic Shock and Experimental Endotoxaemia): Biochemical, Pathophysiological and Therapeutic Aspects," In *Protein Degradation in Health and Disease, Ciba Foundation Symposium* 75:351-379, 1980.

Gilhar and Etzioni, "The Nude Mouse Model for the Study of Human Skin Disorders," *Dermatology* 189:5-8, 1994.

Gooding et al., "Virus Proteins that Counteract Host Immune Defenses" *Cell* 71:5-7, 1992.

Gown et al., "Human Atherosclerosis- Immunocytochemical Analysis of the Cellular Composition of Human Atherosclerotic Lesions," *Am. J. Physiol.* 125:191-207, 1986.

Haber, "Can a Viral Serine Proteinase Inhibitor Prevent Postangioplasty Restenosis?" *Circulation* 94:2694-2695, 1996.

Hagerty and Allen, "Tolerance to Self and the Processing and Presentation of Self Antigens," *Intern. Rev. Immunol.* 10:313-319, 1993.

Hammer et al., "Spontaneous Inflammatory Disease in Transgenic Rates Expressing HLA-B27 and Human β₂m: An Animal Model of HLA-B27-Associated Human Disorders," *Cell* 63:1099-1112, 1990.

Harlan et al., "In Vivo Models of Leukocyte Adherence to Endothelium," in *Adhesion: Its Role in Inflammatory Disease*, Harlan et al. (eds.), W.H. Freeman and Co., New York, 1992, p. 117-150.

Häyry et al., "Chronic Allograft Rejection," *Transplantation Proc.* 28;2337-2338, 1996.

Herzum et al., "Coxsackievirus B3 Infection Leads to Cell Death of Cardiac Myocytes," *J. Mol. Cell. Cardiol.* 26:907-913, 1994.

Hickey et al., "T-Lymphocyte Entry Into the Central Nervous System," *J. Neurosci. Res.* 28:254-260, 1991.

Hill et al., "Soluble Complement Receptor Type 1 Ameliorates the Local and Remote Organ Injury After Intestinal Ischemia-Reperfusion in the Rat," *J. Immunol.* 149:1723-1728, 1992.

Howie and Helyer, "The Immunology and Pathology of NZB Mice," *Adv. Immunol.* 198:215-266, 1968.

Huber and Pfaeffle, "Differential $Th_1$ and $Th_2$ Cell Responses in Male and Female BALB/c Mice Infected with Coxsackievirus Group B Type 3," *J. Virology* 68:5126-5132, 1994.

Jiang and Kanost, "Characterization and Functional Analysis of 12 Naturally Occurring Reactive Site Variants of Serpin-1 from *Manduca Sexta*," *J. Biol. Chem.* 272:1082-1087, 1997.

Jiang et al., "Induction of Indefinite Cardiac Allograft Survival Correlates with Toll-Like Receptor 2 and 4 Downregulation after Serine Protease Inhibitor-1 (SERP-1) Treatment," *Transplantation* 84(9):1158-1167, 2007.

Johnstone et al., "Effects of Intraoperative Radiotherapy on Vascular Grafts in a Canine Model," *Int. J. Radiat. Oncol. Biol. Phys.* 29:1015-1025, 1994.

Kasahara et al., "Autoimmune Myocarditis Induced in Mice by Cardiac C-Protein- Cloning of Complementary DNA Encoding Murine Cardiac C-Protein and Partial Characterization of the Antigenic Peptides," *J. Clin. Invest.* 94:1026-1036, 1994.

Kavanagh et al., "High-Current Stimuli to the Spared Epicardium of a Large Infarct Induce Ventricular Tachycardia," *Circulation* 85:680-698, 1992.

Keelan et al., "Effect of External Abdominal Irradiation on Intestinal Morphology and Brush Border Membrane Enzyme and Lipid Composition," *Radiation Res.* 105:84-96, 1986.

Kelly et al., "Antibody to Intercellular Adhesion Molecule 1 Protects the Kidney Against Ischemic Injury," *Proc. Natl. Acad. Sci. U.S.A.* 91:812-816, 1994.

Kiberd and Young, "Modulation of Glomerular Structure and Function in Murine Lupus Nephritis by Methylprednisolone and Cyclophosphamide," *J. Lab. Clin. Med.* 124:496-506, 1994.

Klinkert et al., "Surface Proteins of *Mycoplasma Hyopneumoniae* Identified from an *Escherichia coli* Expression Plasmid Library," *Infect. Immunity* 49:329-335, 1985.

Kodama et al., "Rat Dilated Cardiomyopathy After Autoimmune Giant Cell Myocarditis," *Circ. Res.* 75:278-284, 1994.

Kouwenhoven et al., "Etiology and Pathophysiology of Chronic Transplant Dysfunction," *Transplant Int.* 13:385-401, 2000.

Kung et al., "Characterization of a Murine Model of Allergic Pulmonary Inflammation," *Int. Arch. Allergy Immunol.* 105:83-90, 1994.

Kusumoto et al., "Role of Endogenous Endothelin in Extension of Rabbit Myocardial Infarction," *J. Cardiovasc. Pharmacol.* 22:S339-S342, 1993.

LeDuc and Nast, "Chemotactic Peptide-Induced Acute Colitis in Rabbits," *Gastroenterology* 98:929-935, 1990.

Libby et al., "A Cascade Model for Restenosis—A Special Case of Atherosclerosis Progression," *Circulation* 86(Suppl. 3):47-52, 1992.

Liu et al., "A Novel Viral Anti-Inflammatory Protein, SERP-1, Reduces Intimal Hyperplasia in Cholesterol-Fed Rabbits After Balloon Angioplasty," *Circulation* 88:I81, 1993. Abstract 0420.

Lomas et al., "Inhibition of Plasmin, Urokinase, Tissue Plasminogen Activator, and $C_{1S}$ by a Myxoma Virus Serine Proteinase Inhibitor," *J. Biol. Chem.* 268:516-521, 1993.

Lowrance et al., "Spontaneous Elaboration of Transforming Growth Factor β Suppresses Host Defense Against Bacterial Infection in Autoimmune MRL/lpr Mice," *J. Exp. Med.* 180:1693-1703, 1994.

Lucas et al., "Virus-Encoded Serine Proteinase Inhibitor SERP-1 Inhibits Atherosclerotic Plaque Development After Balloon Angioplasty," *Circulation* 94:2890-2900, 1996.

Lucas et al., "A Unique Viral Anti-Inflammatory Protein, SERP-1, Reduces Intimal Hyperplasia in Cholesterol-Red Rabits After Angioplasty," J. Cell. Biochem. Suppl. 18A:286, 1994. Abstract E 315.

Macen et al., "SERP1, a Serine Proteinase Inhibitor Encoded by Myxoma Virus, is a Secreted Glycoprotein that Interferes with Inflammation," *Virology* 195:348-363, 1993.

Maksymowych et al., "Amelioration of Established Antigen-Induced Arthritis in Rabbits Treated with a Secreted Viral Serine Proteinase Inhibitor," *J. Rheumatol.* 23:878-882, 1996.

Martorana et al., "Antiischemic Effects of Pirsidomine, a New Nitric Oxide Donor," *Eur. J. Pharmacol.* 257:267-273, 1994.

Mathison et al., "Platelet Activating Factor and Systemic Anaphylasix in *Nippostrongylus Brasiliensis*-Sensitized Rats: Differential Effects of PAF Antagonists," *Br. J. Pharamcol.* 106:263-266, 1992.

Mazur et al., "Selective $\alpha_{11b}\beta_3$ Receptor Blockage with Peptide TP9201 Prevents Platelet Uptake on Dacron Vascular Grafts Without Significant Effect on Bleeding Time," *J. Lab. Clin. Med.* 124:589-599, 1994.

McFadden et al., "Interruption of Cytokine Networks by Poxviruses: Lessons from Myxoma Virus," *J. Leukocyte Biol.* 57:731-738, 1995.

McFadden and Graham, "Modulation of Cytokine Networks by Poxvirus: the Myxoma Virus Model," *Virology* 5:421-429, 1994.

McFadden, "Rabbit, Hare, Squirrel and Swine Poxviruses," in *Encyclopedia of Virology*, Webster et al. (eds.), Academic Press, San Diego, CA, 1994, p. 1153-1160.

McFadden, "DNA Viruses that Affect Cytokine Networks," in *Human Cytokines: Their Roles in Disease and Therapy*, Aggarwal et al. (eds.), Blackwell Scientific, Cambridge, MA, p. 401-420, 1995.

The Merck Manual of Diagnosis and Therapy, 17th Edition, Merck Research Laboratories, 1999, pp. 1072-1073.

Mihelcic et al., "Inhibition of Leukocyte L-Selectin Function With a Monoclonal Antibody Attenuates Reperfusion Injury to the Rabbit Ear," *Blood* 84:2322-2328, 1994.

Miller et al., "Introduction: Allograft Coronary Disease," *J. Heart Lung Transplant* 14:S109-S110, 1995.

Miller et al., "Specific Interaction of Lymphocyte Function-Associated Antigen 3 with CD2 Can Inhibit T Cell Responses," *J. Exp. Med.* 178:211-222, 1993.

Mossman et al., "The Myxoma Virus-Soluble Interferon-γ Receptor Homolog, M-T7, Inhibits Interferon-γ in a Species-Specific Manner," *J. Biol. Chem.* 270:3031-3038, 1995.

Mulligan et al., "Role of Leukocyte Adhesion Molecules in Lung and Dermal Vascular Injury After Thermal Trauma of Skin," *Am. J. Pathol.* 144:1008-1015, 1994.

Mulligan et al., "Role of $\beta_1$, $\beta_2$ Integrins and ICAM-1 in Lung Injury After Deposition of IgG and IgA Immune Complexes," *J. Immunol.* 150:2407-2417, 1993.

Mulligan et al., "Role of Leukocyte Adhesion Molecules in Complement-Induced Lung Injury," *J. Immunol.* 150:2401-2406, 1993.

Mulligan et al., "Protective Effects of Soluble CR1 in Complement- and Neutrophil-Mediated Tissue Injury," *J. Immunol.* 148:1479-1485, 1992.

Nakamoto et al., "In Vivo Treatment of Infected Prosthetic Graft Material with Urokinase: An Animal Model," *J. Vasc. Interv. Radiol.* 5:549-552, 1994.

Nash et al., "SERP-1, a Poxvirus-Encoded Serpin, is Expressed as a Secreted Glycoprotein that Inhibits the Inflammatory Response to Myxoma Virus Infection," *Adv. Exp. Med. Biol.* 425:195-205, 1997.

Nash et al., "Inhibitory Specificity of the Anti-Inflammatory Myxoma Virus Serpin, SERP-1," *J. Biol. Chem.* 273:20982-20991, 1998.

Nicoletti et al., "The Effects of Thymopentin on the Development of SLE-Like Syndrome in the MRL/Ipr-Ipr Mouse," *Scand. J. Immunol.* 40:549-556, 1994.

Okuda et al., "Elevated Expression of Transforming Growth Factor-β and Proteoglycan Production in Experimental Glomerulonephritis," *J. Clin. Invest.* 86:453-462, 1990.

Paul et al., "The Efficacy of LFA-1 and VLA-4 Antibody Treatment in Rat Vascularized Cardiac Allograft Rejection," *Transplantation* 55:1196-1199, 1993.

Paul et al., "Macrophage Subpopulations in Normal and Transplanted Heart and Kidney Tissues in the Rat," *Transplantation* 53:157-162, 1992.

Pemberton et al., "Microvascular Effects of Complement Blockade with Soluble Recombinant CR1 on Ischemia/Reperfusion Injury of Skeletal Muscle," *J. Immunol.* 150:5104-5113, 1993.

Penning et al., "The Design and Synthesis of Second Generation Leukotriene $B_4$ ($LTB_4$) Receptor Antagonists Related to SC-41930," *Agents Actions* 39:C11-C13, 1993.

Percy et al., "In Vitro Changes in the Properties of Rabbit Colonic Muscularis Mucosae in Colitis," *Gastroenterology* 104:369-376, 1993.

Peterseim et al., "Stability of the β-Adrenergic Receptor/Adenylyl Cyclase Pathway of Pediatric Myocardium after Brain Death," *J. Heart Lung Transplant.* 13:635-640, 1994.

Podolsky et al., "Attenuation of Colitis in the Cotton-Top Tamarin by Anti-α4 Integrin Monoclonal Antibody," *J. Clin. Invest.* 92:372-380, 1993.

Popovich et al., "Elevation of the Neurotoxin Quinolinic Acid Occurs Following Spinal Cord Trauma," *Brain Res.* 633:348-352, 1994.

Popovich et al., "Differential Expression of MHC Class II Antigen in the Contused Rat Spinal Cord," *J. Neurotrauma* 10:37-46, 1993.

Pretolani et al., "Antibody to Very Late Activation Antigen 4 Prevents Antigen-Induced Bronchial Hyperreactivity and Cellular Infiltration in the Guinea Pig Airways," *J. Exp. Med.* 180:795-805, 1994.

Rabb et al., "The Role of the Leukocyte Adhesion Molecules VLA-4, LFA-1, and Mac-1 in Allergic Airway Response in the Rat," *Am. J. Respir. Crit. Care Med.* 149:1186-1191, 1994.

Rabinovici et al., "Role of Complement in Endotoxin/Platelet-Activating Factor-Induced Lung Injury," *J. Immunol.* 149:1744-1750, 1992.

Ramaswamy et al., "Pathology of Pulmonary Parasitic Migration: Morphological and Bronchoalveolar Cellular Responses Following *Nippostrongylus brasiliensis* Infection in Rats," *J. Parasitol.* 77:302-312, 1991.

Ramos et al., "Difrerences in Non-MHC Alloantigens Promote Tissue Rejection but Fail to Mediate Allogeneic Co-operation and Autoimmunity in Mice Neonatally Injected with Semi-Allogeneic $F_1$ B Cells," *Immunology* 82:287-293, 1994.

Ramzy et al., "Cardiac Allograft Vasculopathy: A Review," *Can. J. Surg.* 48:319-327, 2005.

Remaut et al., "Plasmid Vectors for High-Efficiency Expression Controlled by the $\rho_L$ Promoter of Coliphage Lambda," *Gene* 15:81-93, 1981.

Santing et al., "Dissociation Between Bronchial Hyperreactivity In Vivo and Reduced β-Adrenoceptor Sensitivity In Vitro in Allergen-Challenged Guinea Pigs," *Eur. J. Pharm.* 257:145-152, 1994.

Santoian et al., "Use of the Porous Balloon in Porcine Coronary Arteries: Rationale for Low Pressure and Volume Delivery," *Cath. Cardiovasc. Diag.* 30:348-354, 1993.

Scott et al., "Local Delivery of an Antithrombin Inhibits Platelet-Dependent Thrombosis," *Circulation* 90:1951-1955, 1994.

Shandelya et al., "Soluble Complement Receptor Type 1 Inhibits the Complement Pathway and Prevents Contractile Failure in the Postischemic Heart," *Circulation* 88:2812-2826, 1993.

Singh and Lebedeva, "Interleukin-1 Contributes to High Level IgG Production in the Murine MRL/Ipr Lupus Model," *Immunol. Invest.* 23:281-292, 1994.

Stadius et al., "Local Infusion Balloon Angioplasty to Obviate Restenosis Compared with Conventional Balloon Angioplasty in an Experimental Model of Atherosclerosis," *Am. Heart J.* 126:47-56, 1993.

Strober and Ehrhardt, "Chronic Intestinal Inflammation: An Unexpected Outcome in Cytokine or T Cell Receptor Mutant Mice," *Cell* 75:203-205, 1993.

Stokes et al., "An Electromechanical Spinal Injury Technique with Dynamic Sensitivity," *J. Neurotrauma* 9:187-195, 1992.

Strom et al., Therapeutic Immunology, Austen et al. (Ed), Blackwell Sciences, Cambridge, MA, 1996, pp. 451-456.

Sun et al., "Cardiac Angiotensin Converting Enzyme and Myocardial Fibrosis in the Rat," *Cardiovasc. Res.* 28:1423-1432, 1994.

Sunberg et al., "Full-Thickness Skin Grafts from Flaky Skin Mice to Nude Mice: Maintenance of the Psoriasiform Phenotype," *J. Invest. Dermatol.* 102:781-788, 1994.

Tanaka et al., "An Angiotensin II Receptor Antagonist Reduces Myocardial Damage in an Animal Model of Myocarditis," *Circulation* 90:2051-2055, 1994.

Takahashi et al., "In Vivo Differentiation of Edematous Changes After Stroke in Spontaneously Hypertensive Rats Using Differentiation Weighted MRI," *Acta Neurochir. Suppl.* 60:224-227, 1994.

Teerlink et al., "Role of Endothelin in the Maintenance of Blood Pressure in Conscious Rats with Chronic Heart Failure. Acute Effects of the Endothelin Receptor Antagonist Ro 47-0203 (Bosentan)," *Circulation* 90:2510-2518, 1994.

Theofilopoulos and Dixon, "Murine Models of Systemic Lupus Erythematosus," *Adv. Immunol.* 37:269-390, 1985.

Thomas et al., "Role of Leukocyte CD11/CD18 Complex in Endotoxic and Septic Shock in Rabbits," *J. Appl. Physiol.* 73:1510-1516, 1992.

Tilney, "Thoughts on the Immunobiology of Chronic Allograft Rejection," *Transplantation Proc.* 27:2123-2125, 1995.

Tilney et al., "Serial Analysis of Cytokines, Adhesion Molecule Expression, and Humoral Responses During Development of Chronic Kidney Allograft Rejection in a New Rat Model," *Transplantation Proc.* 25:861-862, 1993.

Tilney et al., "Chronic Rejection—An Undefined Conundrum," *Transplantation* 52:389-398, 1991.

Turner et al., "Poxvirus Serpins" in *Viroceptors, Virokines and Related Immune Modulators Encoded by DNA Viruses*, G. McFadden (ed.), R.G. Landes Company, Georgetown, Texas, 1994, p. 67-88.

Upton et al., "Myxoma Virus and Malignant Rabbit Fibroma Virus Encode a Serpin-Like Protein Important for Virus Virulence," *Virology* 179:618-631, 1990.

Upton and McFadden, "DNA Sequence Homology Between the Terminal Inverted Repeats of Shope Fibroma Virus and an Endogenous Cellular Plasmid Species," *Mol. Cell. Biol.* 6:265-276, 1986.

Upton et al., "A Novel Member of the Serpin Superfamily is Encoded on a Circular Plasmid-Like DNA Species Isolated from Rabbit Cells," *F.E.B.S. Lett.* 207:115-120, 1986.

Uretsky et al., "Development of Coronary Artery Disease in Cardiac Transplant Patients Receiving Immunosuppressive Therapy with Cyclosporine and Prednisone," *Circulation* 76:827-834, 1987.

Vasquez-Martul et al., "Histological Features with Clinical Impact in Chronic Allograft Nephropathy: Review of 66 Cases," *Transplantation Proceed.* 36:770-771, 2004.

Wang et al., "Treatment with a Short Course of LF 15-0195 and Continuous Cyclosporin A Attenuates Acute Xenograft Rejection in a Rat-to-Mouse Cardiac Transplantation Model," *Xenotransplantation* 10:325-336, 2003.

Wang et al., "Serp-1, a Viral Anti-Inflammatory Serpin, Attenuates Acute Xenograft Rejection in a Rat-to-Mouse Cardiac Transplant Model," *Xenotransplantation* 10:506, 2003. Abstract S14.7.

Wilson et al., "The Effect of Low Molecular Weight Heparin on Intimal Hyperplasia in Vein Grafts," *Eur. J. Vasc. Surg.* 8:60-64, 1994.

Wishart et al., "Comparisons of Repetitive- and Single-Insult Ischaemia: Effects on Regional Brain Damage and Behaviour," *NeuroReport* 5:1541-1544, 1994.

Witkowski et al., "In Vivo Estimation of Cardiac Transmembrane Current," *Circ. Res.* 72:424-439, 1993.

Wolinsky et al., "Use of a Perforated Balloon Catheter to Deliver Concentrated Heparin into the Wall of the Normal Canine Artery," *J. Am. Coll. Cardiol.* 15:475-481, 1990.

Yang et al., "Inhibition of Insulitis and Prevention of Diabetes in Nonobese Diabetic Mice by Blocking L-Selectin and Very Late Antigen 4 Adhesion Receptors," *Proc. Natl. Acad. Sci. U.S.A.* 90:10494-10498, 1993.

Yanos et al., "Mechanism of Respiratory Arrest in an Animal Model of Acute Fatal Bronchoconstriction," *J. Appl. Physiol.* 77:236-244, 1994.

Yednock et al., "Prevention of Experimental Autoimmune Encephalomyelitis by Antibodies Against $\alpha 4\beta 1$ Integrin," *Nature* 356:63-66, 1992.

Zamvil et al., "'Lupus-Prone' Mice are Susceptible to Organ-Specific Autoimmune Disease, Experimental Allergic Encephalomyelitis," *Pathobiology* 62:113-119, 1994.

Zhang et al., "Characterization of a Murine Model of Myocarditis Induced by a Reactivated Coxsackievirus B3," *Int. J. Exp. Path.* 75:99-110, 1994.

Zierhut et al., "Pharmacological Actions of SDZ 218-135, A Novel Positive Inotropic Agent," *Cardiovasc. Drugs Ther.* 8:235-244, 1994.

International Search Report for WO 96/30042 dated Sep. 23, 1996.

International Search Report for WO 01/39790 dated Mar. 22, 2001.

International Search Report for WO 01/30379 dated Apr. 12, 2001.

International Search Report for WO 02/026245 dated Jan. 23, 2003.

International Search Report for WO 04/039391 dated Mar. 8, 2004.

\* cited by examiner

SERP-1/CsA Produces Significant Decrease in Endpoint Joint Destruction Versus Control.

SEQUENCE LISTING

```
<160> NUMBER OF SEQ ID NOS: 1

<210> SEQ ID NO 1
<211> LENGTH: 369
<212> TYPE: PRT
<213> ORGANISM: Myxoma virus

<400> SEQUENCE: 1

Met Lys Tyr Leu Val Leu Val Leu Cys Leu Thr Ser Cys Ala Cys Arg
1               5                   10                  15

Asp Ile Gly Leu Trp Thr Phe Arg Tyr Val Tyr Asn Glu Ser Asp Asn
            20                  25                  30

Val Val Phe Ser Pro Tyr Gly Leu Thr Ser Ala Leu Ser Val Leu Arg
        35                  40                  45

Ile Ala Ala Gly Gly Asn Thr Lys Arg Glu Ile Asp Val Pro Glu Ser
    50                  55                  60

Val Val Glu Asp Ser Asp Ala Phe Leu Ala Leu Arg Glu Leu Phe Val
65                  70                  75                  80

Asp Ala Ser Val Pro Leu Arg Pro Glu Phe Thr Ala Glu Phe Ser Ser
                85                  90                  95

Arg Phe Asn Thr Ser Val Gln Arg Val Thr Phe Asn Ser Glu Asn Val
            100                 105                 110

Lys Asp Val Ile Asn Ser Tyr Val Lys Asp Lys Thr Gly Gly Asp Val
        115                 120                 125

Pro Arg Val Leu Asp Ala Ser Leu Asp Arg Asp Thr Lys Met Leu Leu
    130                 135                 140

Leu Ser Ser Val Arg Met Lys Thr Ser Trp Arg His Val Phe Asp Pro
145                 150                 155                 160

Ser Phe Thr Thr Asp Gln Pro Phe Tyr Ser Gly Asn Val Thr Tyr Lys
                165                 170                 175

Val Arg Met Met Asn Lys Ile Asp Thr Leu Lys Thr Glu Thr Phe Thr
            180                 185                 190

Leu Arg Asn Val Gly Tyr Ser Val Thr Glu Leu Pro Tyr Lys Arg Arg
        195                 200                 205

Gln Thr Ala Met Leu Leu Val Val Pro Asp Asp Leu Gly Glu Ile Val
    210                 215                 220

Arg Ala Leu Asp Leu Ser Leu Val Arg Phe Trp Ile Arg Asn Met Arg
225                 230                 235                 240

Lys Asp Val Cys Gln Val Val Met Pro Lys Phe Ser Val Glu Ser Val
                245                 250                 255

Leu Asp Leu Arg Asp Ala Leu Gln Arg Leu Gly Val Arg Asp Ala Phe
            260                 265                 270

Asp Pro Ser Arg Ala Asp Phe Gly Gln Ala Ser Pro Ser Asn Asp Leu
        275                 280                 285

Tyr Val Thr Lys Val Leu Gln Thr Ser Lys Ile Glu Ala Asp Glu Arg
    290                 295                 300

Gly Thr Thr Ala Ser Ser Asp Thr Ala Ile Thr Leu Ile Pro Arg Asn
305                 310                 315                 320

Ala Leu Thr Ala Ile Val Ala Asn Lys Pro Phe Met Phe Leu Ile Tyr
                325                 330                 335

His Lys Pro Thr Thr Thr Val Leu Phe Met Gly Thr Ile Thr Lys Gly
            340                 345                 350
```

```
Glu Lys Val Ile Tyr Asp Thr Glu Gly Arg Asp Asp Val Val Ser Ser
        355                 360                 365
Val
```

METHOD OF TREATING ARTHRITIS WITH SERP-1 AND AN IMMUNOSUPPRESSANT

CROSS REFERENCE TO RELATED APPLICATIONS

The present application claims benefit of U.S. Provisional Application No. 60/236,939 filed Sep. 29, 2000.

FIELD OF THE INVENTION

The present invention relates to the use of a viral protein, SERP-1, and its analogs, and biologically active fragments thereof in combination with an immunosuppressant to treat inflammatory and immune reactions associated with numerous injuries and disease conditions in mammals.

BACKGROUND OF THE INVENTION

The present invention relates to use of a viral protein, SERP-1, its analogs and biologically active fragments thereof in combination with an immunosuppressant in the prevention and treatment of inflammatory and immune reactions associated with numerous injuries and disease conditions.

Inflammation is the body's reaction to injury and infection. Three major events are involved in inflammation: (1) increased blood supply to the injured or infected area; (2) increased capillary permeability enabled by retraction of endothelial cells; and (3) migration of leukocytes out of the capillaries and into the surrounding tissue (hereinafter referred to as cellular infiltration). Roitt et al., *Immunology*, Grower Medical Publishing, New York, 1989. Increased capillary permeability allows larger molecules to cross the endothelium that are not ordinarily capable of doing so, thereby allowing soluble mediators of immunity such as leukocytes to reach the injured or infected site. Leukocytes, primarily neutrophil polymorphs (also known as polymorphonuclear leukocytes, neutrophils or PMNs) and macrophages, migrate to the injured site by a process known as chemotaxis. At the site of inflammation, tissue damage and complement activation cause the release of chemotactic peptides such as C5a. Id. Complement activation products are also responsible for causing degranulation of phagocytic cells, mast cells and basophils, smooth muscle contraction and increases in vascular permeability. Mulligan et al. 1991 *J. Immunol.* 148: 1479-1485.

The traversing of leukocytes from the bloodstream to extravascular sites of inflammation or immune reaction involves a complex but coordinated series of events. At the extravascular site of infection or tissue injury, signals are generated such as bacterial endotoxins, activated complement fragments or proinflammatory cytokines such as interleukin 1 (IL-1), interleukin 6 (IL-6), and tumor necrosis factor (TNF) which activate leukocytes and/or endothelial cells and cause one or both of these cell types to become adhesive. Initially, cells become transiently adhesive (manifested by rolling) and later, such cells become firmly adhesive (manifested by sticking). Adherent leukocytes travel across the endothelial cell surface, diapedese between endothelial cells and migrate through the subendothelial matrix to the site of inflammation or immune reaction. Harlan et al., *Adhesion-Its role in Inflammatory Disease*, W.H. Freeman & Co., New York, 1992.

Although leukocyte traversal of vessel walls to extravascular tissue is necessary for host defense against foreign antigens and organisms, leukocyte-endothelial interactions often have deleterious consequences for the host. For example, during the process of adherence and transendothelial migration, leukocytes release oxidants, proteases and cytokines that directly damage endothelium or cause endothelial dysfunction. Once at the extravascular site, emigrated leukocytes further contribute to tissue damage by releasing a variety of inflammatory mediators.

Moreover, single leukocytes sticking within the capillary lumen or aggregation of leukocytes within larger vessels are responsible for microvascular occlusion and ischemia. Leukocyte-mediated vascular and tissue injury has been implicated in pathogenesis of a wide variety of clinical disorders such as acute and chronic allograft rejection, vasculitis, rheumatoid and other forms of inflammatory based arthritis, inflammatory skin diseases, adult respiratory distress syndrome, ischemia-reperfusion syndromes such as myocardial infarction, shock, stroke, organ transplantation, crush injury and limb replantation. Id.

Many other serious clinical conditions involve underlying inflammatory processes in humans. For example, multiple sclerosis (MS) is an inflammatory disease of the central nervous system. In MS, circulating leukocytes infiltrate inflamed brain endothelium and damage myelin, with resultant impaired nerve conduction and paralysis. Yednock et al., 1992 *Nature* 366:63-66. Systemic lupus erythematosus (SLE) is an autoimmune disease characterized by the presence of tissue damage caused by self antigen directed antibodies. Auto-antibodies bound to antigens in various organs lead to complement-mediated and inflammatory cell mediated tissue damage. Theofilopoubs, A. N. 1992 *Encyclopedia of Immunology*, pp. 1414-1417.

Reperfusion injury is another condition associated with activation of the inflammatory system and enhanced leukocyte-endothelial cell (EC) adhesion. There is much evidence that adhesion-promoting molecules facilitate interactions between leukocytes and endothelial cells and play important roles in acute inflammatory reaction and accompanying tissue injury. For example, in acute lung injury caused by deposition of IgG immune complexes or after bolus i.v. infusion of cobra venom factor (CVF), neutrophil activation and the generation of toxic oxygen metabolites cause acute injury. Mulligan et al., 1992 *J. Immunol.* 150(6):2401-2405. Neutrophils (PMNs) are also known to mediate ischemia/reperfusion injury in skeletal and cardiac muscle, kidney and other tissues. Pemberton et al., 1993 *J. Immunol.* 150:5104-5113.

Infiltration of airways by inflammatory cells, particularly eosinophils, neutrophils and T lymphocytes are characteristic features of atopic or allergic asthma. Cotran et al., *Pathological Basis of Disease*, W. B. Saunders, Philadelphia, 1994. Cellular infiltration of the pancreas with resultant destruction of islet beta-cells is the underlying pathogenesis associated with insulin-dependent diabetes mellitis. Burkly et al. 1994 *Diabetes* 43: 529-534. Activation of inflammatory cells whose products cause tissue injury underlies the pathology of inflammatory bowel diseases such as Crohn's disease and ulcerative colitis. Cotran et al., 1994. Neutrophils, eosinophils, mast calls; lymphocytes and macrophages contribute to the inflammatory response. Minute microabcesses of neutrophils in the upper epithelial layers of the dermis accompany the characteristic epidermal hyperplasia/thickening and scaling in psoriasis.

Various anti-inflammatory drugs are currently available for use in treating conditions involving underlying inflammatory processes. Their effectiveness however, is widely variable and there remains a significant clinical unmet need. This is especially true in the aforementioned diseases where available therapy is either of limited effectiveness or is accompanied by unwanted side effect profiles. Moreover, few clinical agents are available which directly inhibit cellular infiltration, a major underlying cause of tissue damage associated with inflammation. Thus, there is a need for a safe, effective clinical agent for preventing and ameliorating cellular infiltration and consequential pathologic conditions associated with inflammatory diseases, injuries and resultant perturbations of cytokine networks.

Serine proteinase inhibitors (hereinafter "serpins") make up a superfamily of related proteins and have been found encoded by poxviruses from four different genera. Myxoma virus (MYX) is a leporipoxvirus that causes a virulent systemic infection, myxomatosis, in the European rabbit (*Oryctolagus cuniculus*). Significantly, myxomatosis is characterized by rapid disseminated infection, immunosuppression, and the presence of secondary, gram negative infections. A closely related leporipoxvirus, Shope fibroma virus (SFV), causes only a localized infection in the same host. SFV differs from the virulent myxoma virus in that it contains only a fragmented open reading frame (ORF) for a corresponding myxoma virus ORF designated SERP-1. A disruption of the SERP-1 ORF in myxoma virus or in the related malignant rabbit fibroma virus (MRV) results in attenuation of virus pathogenicity in *O. cuniculus*. Macen et al., 1993 *Virology* 195:348-363. Thus, SERP-1 has been generally implicated in the complex response to leporipoxyiral infection in its natural host, *O. cuniculus*. Although the absence of SERP-1 from myxoma virus apparently causes an increased immune response in rabbit, the mechanism by which SERP-1 acts as a virulence factor is unclear.

The SERP-1 polypeptide has been demonstrated to decrease intimal fatty cellular proliferation associated with restenosis in rabbits following balloon angioplasty. Lucas et al., 1994 *J. Cell. Biochem. Suppl.* 18A:286; Liu et al., 1993 *Circulation* 88:I-81.

It has been discovered in accordance with the present invention that the combination of SERP-1, SERP-1 analogs and biologically active fragments thereof and an immunosuppressant is capable of directly inhibiting the infiltration of tissue by inflammatory cells that are responsible for tissue damage in inflammatory diseases and disorders.

SUMMARY OF THE INVENTION

In accordance with the present invention, it has been surprisingly discovered that the protein SERP-1, a serine protease inhibitor produced by malignant rabbit fibroma virus (MRV) and myxoma virus (MYX), its analogs and biologically active fragments thereof, in combination with an immunosuppressant prevents and reduces infiltration of inflammatory cells in injured and diseased tissues in animals. The present invention therefore, is efficacious for preventing and reducing inflammatory cell infiltration in a diseased or injured tissue of a subject and the physiological symptoms associated therewith.

The present invention provides a method for treating diseases and injuries involving inflammatory and immune reactions. In accordance with the present invention, SERP-1, SERP-1 analogs or biologically active fragments thereof, in combination with an immunosuppressant is administered to a subject in need of such treatment for a time and under conditions sufficient to treat the inflammatory or immune reactions.

One embodiment of the invention is directed to treating inflammatory and immune reactions associated with inflammatory rheumatoid arthritis. Another embodiment of the invention is directed to treating inflammatory and immune reactions associated with systemic lupus erythematosus. Another embodiment is directed to treating inflammatory and immune reactions associated with multiple sclerosis. Yet another embodiment of the invention is directed to treating inflammatory and immune reactions associated with asthma. In all of these embodiments of the invention, the SERP-1, SERP-1 analog or biologically active fragment thereof in combination with an immunosuppressant is delivered in a manner consistent with conventional methodologies associated with treatment of rheumatoid arthritis, systemic lupus erythematosus, multiple sclerosis, and asthma such as for example, intravenously, intra-articularly, intraperitoneally, intra-arterially, intramuscularly, intrarectally, subcutaneously, or by aerosol inhalant in order to inhibit or ameliorate inflammatory and immune reactions associated with such diseases.

Other embodiments of the invention are directed to treating inflammatory and immune reactions associated with injuries and diseases such as: coronary arterial occlusion, cardiac arrhythmias, congestive heart failure, cardiomyopathy, bronchitis, acute allergic reactions and hypersensitivity, neurotrauma, inflammatory bowel diseases, psoriasis, systemic shock injury, myocarditis, insulin dependent diabetes, and stroke. In these embodiments of the invention, the SERP-1, SERP-1 analog or biologically active fragment in combination with an immunosuppressant is delivered in a manner consistent with conventional methodologies associated with treatment of the relevant injury or disease condition such as for example, intravenously, intra-articularly, intra-arterially, intraperitoneally, subcutaneously, intramuscularly, intrarectally, topically or by aerosol inhalant in order to inhibit and ameliorate inflammatory and immune reactions associated with such diseases.

In a further embodiment, the present invention is directed to an article of manufacture comprising packaging material and SERP-1, SERP-1 analog, or biologically active fragment thereof and an immunosuppressant within the packaging material and wherein the pharmaceutical agent is effective for treating inflammatory conditions such as arthritis, inflammatory bowel disease, systemic lupus erythematosus, and multiple sclerosis and wherein the packaging material comprises a label which indicates that the pharmaceutical agent can be used for treating such inflammatory conditions.

These and other objects of the invention are accomplished by the administration of SERP-1, its analogs and biologically active fragments thereof in combination with an immunosuppressant in amounts sufficient to achieve the desired therapeutic effect.

BRIEF DESCRIPTION OF THE DRAWINGS

FIG. 1 is a graph showing the severity of rheumatoid arthritis in animals receiving SERP-1/cyclosporin compared to animals receiving a placebo.

FIG. 2 is a bar graph showing that SERP-1/cyclosporin produces a significant decrease in the severity of established rheumatoid arthritis versus control.

FIG. 3 is a bar graph showing that SERP-1/cyclosporin produces a significant decrease in endpoint joint destruction versus control.

DETAILED DESCRIPTION OF THE INVENTION

In accordance with the present invention, it has been surprisingly discovered that the protein SERP-1, a serine protease inhibitor produced by malignant rabbit fibroma virus (MRV) and myxoma virus (MYX) and the subject of U.S. Pat. No. 5,686,409, its analogs and biologically active fragments thereof in combination with an immunosuppressant is useful for treating the clinical manifestations of infiltration of inflammatory cells in injured or diseased tissues in animals, including humans. For purposes of the present invention, the terms "treat", "treating" or "treatment" includes preventing, inhibiting, reducing the occurrence of and/or ameliorating the physiological effects of infiltration of inflammatory cells in injured and diseased tissues in animals, including humans.

More specifically, in accordance with the present invention, a therapeutically effective amount of SERP-1, SERP1 analogs or biologically active fragments thereof and an immunosuppressant are co-administered to a subject in need of such treatment for a time and under conditions sufficient to treat, for example, rheumatoid arthritis. The term "subject" as used herein is taken to mean any mammalian patient to which the compositions of the invention may be administered. Subjects specifically intended for treatment with the compositions and methodologies of the present invention include humans, as well as non human primates, sheep, horses, cattle, goats, pigs, dogs, cats, rabbits, guinea pigs, poultry, hamsters, rats and mice, as well as the organs, tumors and cells derived or originating from these hosts. Immunosuppressants contemplated by the present invention specifically include but are not limited to cyclosporine (e.g., Cyclosporine A, SANDIMMUNE®, NEORAL®, (Novartis), RAPIMMUNE® (American Home Products), FK501 (Fijisawa), CELLCEPT® (Roche, Syntex), IMUREK®, SPANIDIN® and PROGRAF®.

The present invention, therefore, is useful for treatment of a variety of clinical conditions involving inflammatory pathologies such as inflammatory arthritis. There are many different types of arthritis clinically recognized, the most common being rheumatoid arthritis. However, the inflammatory pathway relevant to the pathogenesis of rheumatoid arthritis is also likely relevant to the pathogenesis of other types of arthritis e.g. osteo, psoriatic and spondyloarthropathies since the synovial pathologies in all these forms of arthritis is in many cases, the same.

Adult respiratory distress syndrome (ARDS) is also treatable with the compositions and methodologies of the present invention. ARDS is an inflammatory condition characterized by increased capillary permeability, interstitial and: intraalveolar edema, fibrin exudation and formation of hyaline membrane. Inflammatory cells and mediators including leukocytes, cytokines, oxygen radicals, complement and arachidonate metabolite damage capillary endothelium and allow fluid and protein to leak across capillaries.

The present invention is also useful for treating inflammatory and immune reactions associated with systemic lupus erythematosus (SLE). SLE is a classical multisystem autoimmune disease characterized by the presence of tissue damage due to self antigen directed antibodies. Autoantibodies bound to antigens in various organs lead to complement-mediated and inflammatory cell mediated tissue damage. Skin, connective tissue, blood vessels, and joints are all effected in this chronic, remitting and relapsing disease, but kidney failure due to antibody mediated glomerulonephritis is the main life-threatening complication. The present invention is useful in treating other autoimmune disorders such as Scleroderma, various forms of vasculitis, inflammatory autoimmune myositis, and autoimmune thyroiditis.

The compositions and methodologies of the present invention are also efficacious in the treatment of multiple sclerosis (MS). M.S. is characterized by the penetration of the blood-brain barrier by circulating leukocytes, leading to demyelination in various parts of the brain, impaired nerve conduction and, ultimately, paralysis. Certain T cell clones reactive to myelin basic protein localize in the central nervous system and initiate inflammation.

In the aforementioned embodiments of the invention, the SERP-1, SERP-1 analog or biologically active fragment thereof is delivered together with an immunosuppressant e.g., Cyclosporine A in a manner consistent with conventional methodologies associated with the treatment of, for example, rheumatoid arthritis, systemic lupus erythematosus, inflammatory autoimmune myositis, autoimmune thyroiditis, and multiple sclerosis such as for example, intravenously, intraarticularly, intrarectally, intraperitoneally, intramuscularly, subcutaneously, or by aerosol inhalant in order to prevent inflammatory and immune reactions associated with such diseases.

The present invention is useful for treating many other clinical conditions involving inflammatory processes. For example, inflammatory bowel diseases including Crohn's disease and ulcerative colitis are spontaneous chronic inflammations of the gastrointestinal tract which involve activation of inflammatory cells whose products cause tissue injury. Neutrophils, eosinophils, mast cells, lymphocytes and macrophages contribute to the inflammatory response. Weight gain, stool consistency and cecum size are parameters which can be used to assess the effects of SERP-1/immunosuppressant treatment in animals, including humans. Psoriasis which is characterized by, among other symptoms, epidermal hyperplasia/thickening and minute microabcesses of neutrophils in the upper epithelial layers of the dermis, is also treatable by the compositions and methodologies of the present invention. Psoriasis is believed to be caused by an autoimmune inflammatory response to a set of antigens in the skin. An increased autologous T cell response is seen in cells derived from a psoriatic lesion.

The present invention is also directed to treatment of systemic shock and many resultant clinical conditions associated therewith. Systemic shock often occurs as a complication of severe blood loss, severe localized bacterial infection, ischemia/reperfusion trauma and is a major cause of death in intensive care units. Most cases of septic shock are induced by endotoxins (i.e., bacterial cell wall lipopolysaccharides or LPS) from gram negative bacilli or toxins (i.e., toxic shock toxin 1) from gram positive cocci bacteria. The release of LPS in the bloodstream causes release of inflammatory mediators (inflammatory cytokines, platelet activating factor, complement, leukotrienes, oxygen metabolites, and the like) which cause myocardial dysfunction, vasodilation, hypotension, endothelial injury, leukocyte adhesion and aggregation, disseminated intravascular coagulation, adult respiratory distress syndrome (ARDS), liver, kidney and central nervous system (CNS) failure. Shock due to blood loss also involves inflammatory mediator release. In each case, inflammatory responses are induced at the original site of trauma, and also in the vasculature and remote vascularized sites.

Myocardial ischemia is associated with activation of the complement system which further promotes cardiac injury with the enhancement of a series of inflammatory events. Life threatening local and remote tissue damage occurs during surgery, trauma and stroke when major vascular beds are deprived for a time of oxygenation (ischemia), then restored with normal circulation (reperfusion). Reperfusion injury is characterized by vascular permeability leading to edema and infiltration of inflammatory cells. Neutrophils contribute significantly to reperfusion damage by generating oxidants or releasing proteases that damage the microvasculature or adjacent tissue. Cell death and tissue damage due to complement and inflammatory cell mechanisms lead to organ failure or decreased organ function. The activation of mediators by a local injury can also cause a remote injury to highly vascularized organs. The compositions and methodologies of the present invention are useful in the treatment of ischemia and reperfusion injury.

Inflammatory response damage also occurs in glomerulonephritis as well as tubule disease. Infiltration of inflammatory cells (especially macrophages) is linked to proteinuria accompanied histologically by hypercellularity and crescent formation in glomeruli. Over a longer term, the infiltration of inflammatory cells is associated with accumulation of extracellular matrix and sclerosis and chronic compromise of renal function. The present invention is also efficacious in treating glomerulonephritis and tubule disease.

There are many other disease and injury conditions which benefit from the compositions and methodologies of the present invention such as for example, coronary arterial occlusion, cardiac arrhythmias, congestive heart failure, cardiomyopathy, bronchitis, acute allergic reactions and hypersensitivity, neurotrauma, myocarditis, insulin dependent diabetes, and stroke.

In accordance with the present invention, the aforementioned disease and injury conditions are treated by administering the SERP-1, SERP-1 analog or biologically active fragment thereof in combination with an immunosuppressant in a manner consistent with conventional methodologies associated with treatment of the relevant injury or disease condition such as for example, intravenously, intra-articularly, intraperitoneally, topically, intrarectally, intra-arterially, intramuscularly, subcutaneously or by aerosol inhalant in order to treat inflammatory and immune reactions associated with such disease and injury conditions.

In accordance with the present invention, the SERP-1 protein, SERP-1 analog or biologically active fragment thereof, is first obtained and purified in accordance with the teachings of U.S. Pat. Nos. 5,686,409 and 5,939,525, whose teaching are incorporated by reference (i.e., SERP-1 protein comprising a sequence of SEQ ID NO: 1).

After purification to a semi-pure or preferably to the more highly purified state, SERP-1 may then be admixed with sterile water and saline or other pharmaceutically acceptable carrier to a concentration in the range of between 1 pg/ml and 10 mg/ml and preferably between 1 pg/ml and 1 ug/ml. Alternatively, the SERP-1, SERP-1 analog, or biologically active fragment thereof, may be stored as a lyophilized powder, or frozen, and then later solubilized in sterile water or saline or other pharmaceutically acceptable carrier to the above delineated concentrations.

The SERP-1 of the present invention may be administered to a human patient preferably as a pharmaceutical composition in a therapeutically effective amount. It is contemplated that a therapeutically effective amount of an immunosuppressant can be administered from about 1 to about 60 days prior to administration of a therapeutically effective amount of SERP-1 alone and/or SERP-1 together with the immunosuppressant, to achieve the desired treatment.

The term "therapeutically effective amount" means the dose needed to effectively treat the physiological effects of, for example, rheumatoid arthritis. The pharmaceutical compositions of the present invention contain a therapeutically effective dose of the SERP-1 protein, homologs or analogs thereof or else contain a biologically active fragment of the SERP-1 protein, homologs or analogs thereof together with an immunosuppressant and a pharmaceutically acceptable carrier.

As used herein, "analogs" is meant to include substitutions or alterations in the amino acid sequence of the SERP-1 protein, which substitutions or alterations (e.g., additions and deletions) maintain the anti-inflammatory properties of the protein when delivered to the site of inflammation either directed at the site, i.e. locally, or systemically.

For purposes of the present invention, the term "analog" includes amino acid insertional derivatives of SERP-1 such as amino and/or carboxyl terminal fusions as well as intra-sequence insertions of single or multiple amino acids. Insertional amino acid sequence variants are those in which one or more amino acid residues are introduced into a predetermined site in the protein. Random insertion is also possible with suitable screening of the resulting product. Deletional variants are characterized by removal of one or more amino acids from the sequence. Substitutional amino acid variants are those in which at least one residue in the sequence has been removed and a different residue inserted in its place. Where the protein is derivatized by amino acid substitution, amino acids are generally replaced by other amino acids having similar physical chemical properties such as hydrophobicity, hydrophilicity, electronegativity, bulky side chains and the like. Examples of conservative substitutions include the substitution of a non-polar (hydrophobic) residue such as isoleucine, valine, leucine or methionine for another. Likewise, the present invention contemplates the substitution of a polar (hydrophilic) residue such as between arginine and lysine, between glutamine and asparagine, and between glycine and serine. Additionally, the substitution of a basic residue such as lysine, arginine or histidine for another or the substitution of an acidic residue such as aspartic acid or glutamic acid for another is also contemplated.

As used herein, the term "analogs" also encompasses homologs of SERP-1, i.e., corresponding amino acid sequences derived from other SERP-1 proteins and having the same or substantially the same anti-inflammatory properties. As used herein, the term "biologically active fragments" refer to fragments of SERP-1 or SERP-1 analogs which do not encompass the entire length of the SERP-1 polypeptide but which nevertheless maintain the anti-inflammatory properties of the entire SERP-1 polypeptide or analogs thereof when delivered to the site of inflammation either at the site (i.e. locally) or systemically.

SERP-1 amino acid variants may be readily made using peptide synthetic techniques well known in the art such as solid phase peptide synthesis (Merrifield synthesis) and the like or by recombinant DNA techniques well known in the art. Techniques for making substitution mutations at predetermined sites in DNA include for example M13 mutagenesis. Manipulation of DNA sequences to produce substitutional, insertional, or deletional variants are conveniently described elsewhere such as Sambrook et al., 1989 Molecular Cloning: A Laboratory Manual, Cold Spring Harbor Laboratories, Cold Spring Harbor, N.Y.

For purposes of the present invention, analogs of SERP-1 also include single or multiple substitutions, deletions and/or additions of any (component(s) naturally or artificially associated with the SERP-1 such as carbohydrate, lipid and/or other proteinaceous moieties. All such molecules are encompassed by the term SERP-1 analogs.

In one embodiment of the invention, in order to increase the specific activity of the prepared SERP-1 protein, the cysteine residue at position 244 may be substituted with another amino acid residue, for example alanine. Such a substitution causes the SERP-1 protein to be more biologically active since $Cys_{244}$ is the predicted position for SERP-1 dimer formation through disulfide bridges. Because $cys^{244}$ lies very close to the reactive center of the SERP-1 protein, SERP-1 dimers are thought to have a disturbed and obfuscated reactive center thereby rendering them biologically inactive. Lomas et al., 1993 J. Biol. Chem. 268 (1): 516-521. A mutation at position 244 prevents the formation of SERP-1 dimers in the production of SERP-1 through recombinant DNA means. A decrease in the presence of SERP-1 dimers in a preparative sample is useful since the specific activity of the isolated protein will be increased and thus less protein will be needed in a pharmaceutical preparation. The inhibitory activity of serpins on serine proteinases is believed to revolve around the slow dissociation of the serpin from the serine protease after cleavage of the serpin between the P1 and P1' residues in the active region. Upton et al., 1990 Virology 179: 618-631. The amino acid sequence Arg/Asp has been located at the predicted SERP-1 P1-P1' site (amino acid residues 319 and 320) and is the predicted site for cleavage by serine proteases. Substitutions of either or both of these two amino acids produces SERP-1 analogs of varying biological activities useful in the practice of the present invention.

The formulation of pharmaceutical compositions is generally known in the art and reference can conveniently be made to Remington's Pharmaceutical Sciences, 17th ed., Mack Publishing Co., Easton, Pa. Formulation of the SERP-1 protein, analogs, or fragments thereof for use in the present invention must be stable under the conditions of manufacture and storage and must also be preserved against the contaminating action of microorganisms such as bacteria and fungi. Prevention against microorganism contamination can be achieved through the addition of various antibacterial and antifungal agents.

The pharmaceutical forms of SERP-1 suitable for infusion include sterile aqueous solutions or dispersions and sterile powders for the extemporaneous preparation of sterile injectable solutions or dispersion. In all cases, the form must be sterile and must be fluid to the extent that easy syringability exists. Typical carriers include a solvent or dispersion medium containing; example, water buffered aqueous solutions (i.e., biocompatible buffers), ethanol, polyols such as glycerol, propylene glycol, polyethylene glycol, suitable mixtures thereof, surfactants, or vegetable oils. Sterilization can be accomplished by any art-recognized technique, including but not limited to filtration or addition of antibacterial or antifungal agents, for example, paraben, chlorobutanol, phenol, sorbic acid or thimerosal. Further, isotonic agents such as sugars or sodium chloride may be incorporated in the subject compositions.

Production of sterile injectable solutions containing the subject SERP-1/immunosuppressant is accomplished by incorporating these compounds in the required amount in the appropriate solvent with various ingredients enumerated above, as required, followed by sterilization, preferably filter sterilization. To obtain a sterile powder, the above solutions are vacuum-dried or freeze-dried as necessary.

The SERP-1 protein or analogs and fragments thereof, are thus compounded for convenient and effective administration in pharmaceutically effective amounts with a suitable pharmaceutically acceptable carrier in a therapeutically effective dose.

As used herein, the term "pharmaceutically acceptable carrier and/or diluent" includes any and all solvents, dispersion media, antibacterial and antifungal agents, microcapsules, liposomes, cationic lipid carriers, isotonic and absorption delaying agents and the like which are not incompatible with the active ingredients (SERP-1, SERP-1 analogs and fragments thereof). The use of such media and agents for pharmaceutical active substances is well known in the art. Supplementary active ingredients may also be incorporated into the compositions and used in the methods of the present invention.

The precise therapeutically effective amount of SERP-1/immunosuppressant to be used in the methods of this invention applied to humans can be determined by the ordinarily skilled artisan with consideration of individual differences in age, weight, extent of cellular infiltration by inflammatory cells and condition of the patient. It can generally be stated that the SERP-1/immunosuppressant pharmaceutical preparation of the present invention should be preferably administered in an amount of at least about 1 pg/kg to about 5 g/kg per infusion dose, more preferably in an amount of about 5 µg/kg to about 50 mg/kg per dose. It is also contemplated that SERP-1 and an immunosuppressant may be administered in sequential order. In this case, SERP-1 is administered in an amount of at least about 5 µg/kg per infusion dose to about 5 g/kg per infusion dose and preferably in an amount of about 50 µg/kg to about 50 mg/kg per infusion dose. An immunosuppressant is administered in an amount of at least about 1 mg/kg to about 50 mg/kg per infusion dose and preferably in an amount of about 4 mg/kg per infusion dose.

It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active material calculated to produce the desired therapeutic effect in association with the required pharmaceutical carrier. The specification for the novel dosage unit forms of the invention are dictated by and directly depend on the unique characteristics of the active material (e.g., SERP-1 protein, Cyclosporine A, Neoral®, FK501, Rapimmune®) and the limitations inherent in the art of compounding such an active material for the treatment of transplant rejection as herein disclosed in detail.

The principal active ingredients are compounded for convenient and effective administration in effective amounts with a suitable pharmaceutically acceptable carrier in dosage unit form as hereinabove disclosed. A unit dosage form can, for example, contain the principal active compound in amounts ranging from about 5 µg/kg to about 500 mg/kg. The immunosuppressant (e.g. Cyclosporine A) or combinations of immunosuppressants (e.g., Cyclosporine A and FK501) are contained in a unit dosage form in amounts ranging from about 1 mg/kg to about 100 mg/kg. Where combinations of immunosuppressants are employed, it is contemplated that the total unit dosage form of such agents ranges from about 1 mg/kg to about 500 mg/kg. In the case of compositions containing supplementary active ingredients, the dosages are determined by reference to the usual dose and manner of administration of the ingredients.

Packaging material used to contain the SERP-1 active ingredient can comprise glass, plastic, metal or any other suitable inert material so long as the packaging material does not chemically react with any of the ingredients contained therein.

The SERP-1 protein, analogs or fragments thereof may be administered in a manner compatible with the dosage formulation and in such amount as will be therapeutically effective. The compositions of the invention may be administered in any way which is medically acceptable which may depend on the disease condition or injury being treated. Possible administration routes include injections, by parenteral routes such as intravascular, intravenous, intra-arterial, subcutaneous, intramuscular, intratumor, intraperitoneal, intraventricular, intraepidural or others, as well as oral, nasal, ophthalmic, rectal, topical, or by inhalation. The compositions may also be directly applied to tissue surfaces during surgery. Sustained release administration is also specifically included in the invention, by such means as depot injections or erodible implants.

The invention is further illustrated by the following specific examples which are not intended in any way to limit the scope of the invention.

EXAMPLE 1

Treatment of Collagen-induced Arthritis (CIA) in Rats with SERP-1/Cyclosporin Twenty four rats (Louvain) weighing 125-150 g were housed at the UCLA vivarium facility and were fed standard laboratory chow and water.

Arthritis Induction:

Type II collagen, (CII) was prepared by pepsin treatment of chick sternal cartilage or was purchased from Genzyme (Boston, Mass.). Rats were anesthetized with ether and were immunized intradermally at several sites on the back, with 0.5 mg native CII solubilized in 0.1M acetic acid and emulsified in FIA (Difco, Detroit, Mich.). The signs and symptoms of rheumatoid arthritis developed over a period of ten days after immunization with collagen. (Oliver and Brahn, (1996) *J. Rheumatol.* 23, S44-56-60, incorporated herein by reference).

CsA Administration/Osmotic Pumps:

Cyclosporin at (4 mg/kg/d; sc) was administered by osmotic pump for the duration of the study.

SERP-1 Administration:

SERP-1 (0.5 mg/kg) was administered by daily intravenous injections beginning on the day of disease onset (day 10) until the study termination (day 28).

Figure 2:
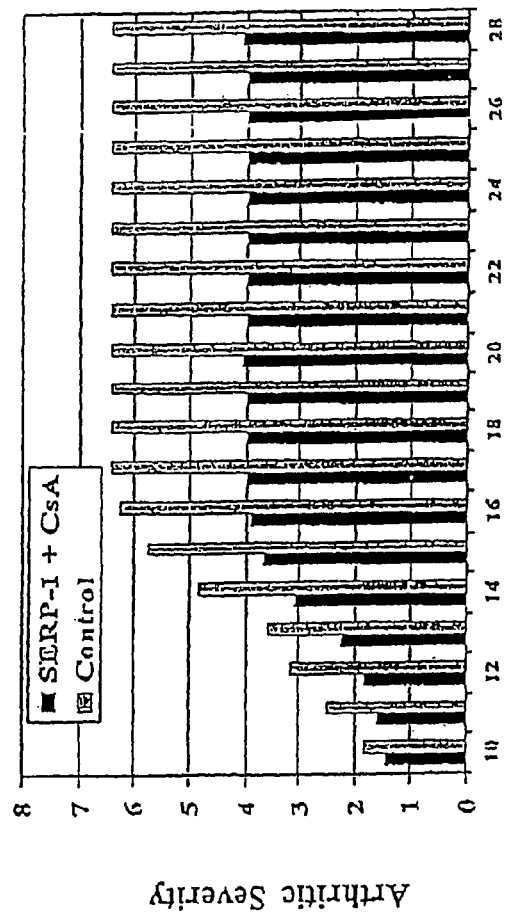
Figure 3:
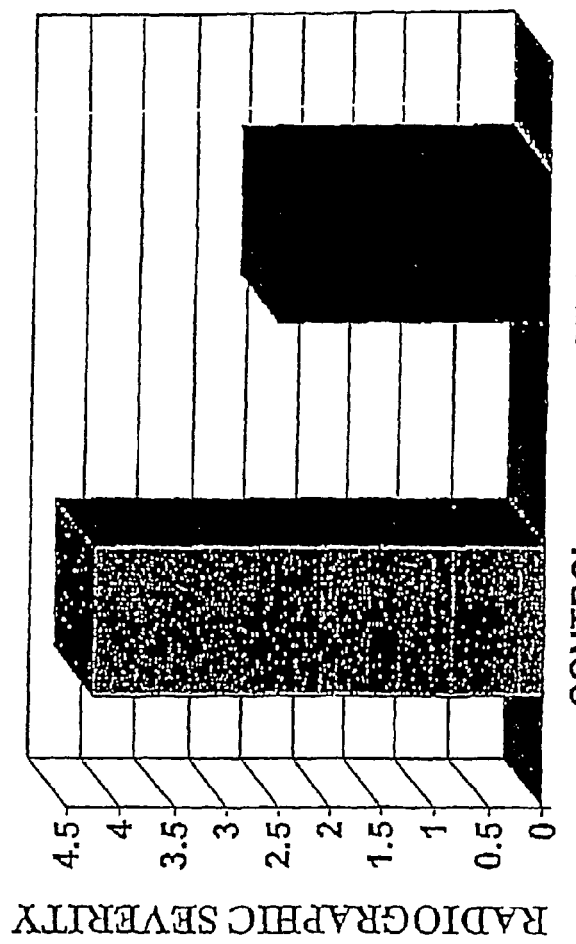

Study Endpoints:

The incidence and severity of chronic arthritis in SERP-1/CsA treated and untreated rats was evaluated via a number of study endpoints. During the experimental phase of the study, the individual hind limbs of each rat was evaluated daily and arthritis severity was quantified by assigning a score (0=normal, 4=maximum/hindpaw) based on increasing levels of swelling and periarticular erythema. The daily, arthritic severity scores for each rat were recorded from disease onset (day 10) until study termination (Table 1). Arthritic severity was significantly lower for the SERP-1/cyclosporin treated group in comparison to controls (p<0.006 based on comparison of AUC; FIG. 2). At the study termination, blinded radiographic scoring (0=normal, 3=maximal/hindpaw) of the ankle joint was performed. The criteria for scoring were the extent of joint space narrowing, bone destruction, periosteal new bone formation and soft tissue swelling (FIG. 3). The mean radiographic scores for each rat are presented in the last column of Table 1. Subjects within the SERP-1 treated group had significantly less joint erosions than the control group ($2.58 \pm 1.88$ vs. $4.27 \pm 1.68$, respectively; p=0.02).

These results demonstrate that administration of purified SERP-1/cyclosporin in an animal model of arthritis results in a considerable diminution in chronic inflammatory cell infiltration as well as a considerable diminution in the radiographic severity of joint destruction compared to controls.

TABLE 1

| VIRON: SERP 1/CYCLOSPORIN COMBO | | | | | | | | | |
|---|---|---|---|---|---|---|---|---|---|
| 3/13/2000 CONTROL: PBS I.v + PEG Pump | day 10 | day 11 | day 12 | day 13 | day 14 | day 15 | day 16 | day 17 | day 18 |
| LA Cage I | 2 | 2 | 3 | 3 | 5 | 7 | 8 | 8 | 8 |
| LT | 2 | 2 | 2 | 2 | 3 | 4 | 5 | 5 | 5 |
| LP | 2 | 3 | 4 | 4 | 5 | 5 | 5 | 5 | 5 |
| RA | 2 | 2 | 3 | 4 | 5 | 5 | 5 | 5 | 5 |
| RT | 1 | 2 | 2 | 3 | 5 | 7 | 8 | 8 | 8 |
| RP | 1 | 1 | 1 | 2 | 3 | 4 | 4 | 4 | 4 |
| LA Cage II | 2 | 3 | 4 | 4 | 5 | 5 | 5 | 5 | 5 |
| LT | 2 | 3 | 4 | 4 | 5 | 5 | 5 | 5 | 5 |
| LP | 2 | 3 | 4 | 4 | 5 | 6 | 7 | 8 | 8 |
| RA | 2 | 2 | 4 | 5 | 6 | 7 | 8 | 8 | 8 |
| LT | 2 | 3 | 3 | 4 | 6 | 8 | 8 | 8 | 8 |
| LP | 2 | 4 | 4 | 5 | 6 | 6 | 7 | 8 | 8 |
| Control Mean Score | 1.833333 | 2.5 | 3.166667 | 3.583333 | 4.833333 | 5.75 | 6.25 | 6.416667 | 6.416667 |
| Standard Deviation | 0.389249 | 0.797724 | 1.029857 | 0.996205 | 1.029857 | 1.288057 | 1.544786 | 1.676486 | 1.676486 |
| Standard Error (SD/sqrIN) | 0.11237 | 0.23029 | 0.297303 | 0.287588 | 0.297303 | 0.371841 | 0.445954 | 0.483974 | 0.483974 |
| 3/13/2000 CONTROL: PBS I.v + PEG Pump | day 19 | day 20* | day 21 | day 22 | day 23 | day 24 | day 25 | day 26 | day 27 | day 28 |
| LA Cage I | 8 | 8 | 8 | 8 | 8 | 8 | 8 | 8 | 8 | 8 |
| LT | 5 | 5 | 5 | 5 | 5 | 5 | 5 | 5 | 5 | 5 |
| LP | 5 | 5 | 5 | 5 | 5 | 5 | 5 | 5 | 5 | 5 |
| RA | 5 | 5 | 5 | 5 | 5 | 5 | 5 | 5 | 5 | 5 |
| RT | 8 | 8 | 8 | 8 | 8 | 8 | 8 | 8 | 8 | 8 |
| RP | 4 | 4 | 4 | 4 | 4 | 4 | 4 | 4 | 4 | 4 |
| LA Cage II | 5 | 5 | 5 | 5 | 5 | 5 | 5 | 5 | 5 | 5 |
| LT | 5 | 5 | 5 | 5 | 5 | 5 | 5 | 5 | 5 | 5 |
| LP | 8 | 8 | 8 | 8 | 8 | 8 | 8 | 8 | 8 | 8 |

TABLE 1-continued

VIRON: SERP 1/CYCLOSPORIN COMBO

| | | | | | | | | | | |
|---|---|---|---|---|---|---|---|---|---|---|
| RA | 8 | 8 | 8 | 8 | 8 | 8 | 8 | 8 | 8 | 8 |
| LT | 8 | 8 | 8 | 8 | 8 | 8 | 8 | 8 | 8 | 8 |
| LP | 8 | 8 | 8 | 8 | 8 | 8 | 8 | 8 | 8 | 8 |
| Control Mean Score | 6.416667 | 6.416667 | 6.416667 | 6.416667 | 6.416667 | 6.416667 | 6.416667 | 6.416667 | 6.416667 | 6.416667 |
| Standard Deviation | 1.676486 | 1.676486 | 1.676486 | 1.676486 | 1.676486 | 1.676486 | 1.676486 | 1.676486 | 1.676486 | 1.676486 |
| Standard Error (SD/sqrIN) | 0.483974 | 0.483974 | 0.483974 | 0.483974 | 0.483974 | 0.483974 | 0.483974 | 0.483974 | 0.483974 | 0.483974 |

| 3/13/2000 CONTROL: PBS I.v + PEG Pump | Start Wt 2/24/2000 | Final Wt 3/13/2000 | Della Wt | DTH | AnlI-Cll Antibody | X-Ray Score |
|---|---|---|---|---|---|---|
| LA Cage I | 148 | | | | | |
| LT | 147 | 143.4 | −3.6 | | 0.426 | 2 |
| LP | 140 | 146.5 | 6.5 | | 0.377 | 3 |
| RA | 150 | 140.4 | −9.6 | | 0.431 | 3 |
| RT | 138 | 131.6 | −6.4 | | 0.509 | 6 |
| RP | 143 | 143.2 | 0.2 | | 0.523 | 3 |
| LA Cage II | 136 | 131.4 | −4.6 | 1.82 | 0.535 | 3 |
| LT | 148 | 138 | −10 | 1.38 | 0.435 | 3 |
| LP | 125 | 116.7 | −8.3 | 2.03 | 0.458 | 6 |
| RA | 132 | 121.7 | −10.3 | 2.09 | 0.415 | 6 |
| LT | 144 | 133 | −11 | 1.17 | 0.332 | 6 |
| LP | 131 | 123.1 | −7.9 | 1.94 | 0.405 | 6 |
| Control Mean Score | 140.1667 | 133.5455 | −5.90909 | 1.738333 | 0.440545455 | 4.272727 |
| Standard Deviation | 7.929615 | 9.832839 | 5.327561 | 0.37616 | 0.062274174 | 1.678744 |
| Standard Error (SD/sqrIN) | 2.28915 | 2.965271 | 1.606623 | 0.153598 | 0.018779908 | 0.506256 |

| SERP-I + Cycosporine Pump | day 10 | day 11 | day 12 | day 13 | day 14 | day 15 | day 16 | day 17 | day 18 |
|---|---|---|---|---|---|---|---|---|---|
| LA Cage III | 2 | 2 | 2 | 3 | 4 | 6 | 7 | 8 | 8 |
| LT | 1 | 1 | 1 | 2 | 3 | 4 | 4 | 4 | 4 |
| LP | 1 | 2 | 2 | 3 | 5 | 6 | 6 | 6 | 6 |
| RA | 2 | 2* | 2 | 3 | 4 | 5 | 5 | 5 | 5 |
| RT | 2 | 2 | 2 | 2 | 3 | 4 | 5 | 5 | 5 |
| RP | | 1 | 1 | 1 | 1 | 1 | 1 | 1 | 1 |
| LA Cage IV | 1 | 1 | 1 | 1 | 2 | 2 | 2 | 2 | 2 |
| LT | 1 | 2 | 3 | 3 | 4 | 4 | 5 | 5 | 5 |
| LP | 1 | 1 | 2 | 3 | 4 | 4 | 4 | 4 | 4 |
| RA | 2 | 2 | 2 | 2 | 2 | 2 | 2 | 2 | 2 |
| RT | | 1 | 1 | 1 | 1 | 1 | 1 | 1 | 1 |
| RP | | 2 | 3 | 3 | 4 | 5 | 5 | 5 | 5 |
| Combo Mean Score | 1.444444 | 1.583333 | 1.833333 | 2.25 | 3.083333 | 3.666667 | 4 | 4 | 4 |
| Standard Deviation | 0.527046 | 0.514929 | 0.717741 | 0.866025 | 1.311372 | 1.775251 | 1.975225 | 2.132007 | 2.132007 |
| Standard Error (SD/sqrIN) | 0.175682 | 0.148651 | 0.2072 | 0.250007 | 0.378572 | 0.512486 | 0.570215 | 0.615476 | 0.615476 |
| P Value By T Test | | 0.001468 | 0.000657 | 0.001014 | 0.00073 | 0.001669 | 0.001955 | 0.002695 | 0.002695 |

| SERP-I + Cycosporine Pump | day 19 | day 20* | day 21 | day 22 | day 23 | day 24 | day 25 | day 26 | day 27 | day 28 |
|---|---|---|---|---|---|---|---|---|---|---|
| LA Cage III | 8 | 8 | 8 | 8 | 8 | 8 | 8 | 8 | 8 | 8 |
| LT | 4 | 4 | 4 | 4 | 4 | 4 | 4 | 4 | 4 | 4 |
| LP | 6 | 6 | 6 | 6 | 6 | 6 | 6 | 6 | 6 | 6 |
| RA | 5 | 5 | 5 | 5 | 5 | 5 | 5 | 5 | 5 | 5 |
| RT | 5 | 5 | 5 | 5 | 5 | 5 | 5 | 5 | 5 | 5 |
| RP | 1 | 0 | 0 | 0 | 0 | 0 | 0 | 0 | 0 | 0 |
| LA Cage IV | 2 | 2 | 2 | 2 | 2 | 2 | 1 | 1 | 1 | 1 |
| LT | 5 | 6 | 6 | 6 | 6 | 6 | 6 | 6 | 6 | 6 |
| LP | 4 | 4 | 4 | 4 | 4 | 4 | 4 | 4 | 4 | 4 |
| RA | 2 | 3 | 3 | 3 | 3 | 3 | 4 | 4 | 4 | 5 |
| RT | 1 | 1 | 0 | 0 | 0 | 0 | 0 | 0 | 0 | 0 |
| RP | 5 | 5 | 5 | 5 | 5 | 5 | 5 | 5 | 5 | 5 |
| Combo Mean Score | 4 | 4.083333 | 4 | 4 | 4 | 4 | 4 | 4 | 4 | 4.083333 |
| Standard Deviation | 2.132007 | 2.274696 | 2.412091 | 2.412091 | 2.412091 | 2.412091 | 2.486326 | 2.486326 | 2.486326 | 2.503028 |
| Standard Error (SD/sqrIN) | 0.615476 | 0.656667 | 0.696331 | 0.696331 | 0.696331 | 0.696331 | 0.717762 | 0.727762 | 0.717762 | 0.717762 |
| P Value By T Test | 0.002695 | 0.004546 | 0.004657 | 0.004657 | 0.004657 | 0.004657 | 0.005317 | 0.005317 | 0.005317 | 0.006793 |

TABLE 1-continued

VIRON: SERP 1/CYCLOSPORIN COMBO

| SERP-I + Cycosporine Pump | Start Wt 2/24/2000 | Final Wt 3/13/2000 | Della Wt | DTH | AnII-Cll Antibody | X-Ray Score |
|---|---|---|---|---|---|---|
| LA Cage III | 148 | 134.8 | −13.2 | 1.22 | 0.397 | 6 |
| LT | 139 | 137.4 | −1.6 | 2.13 | 0.405 | 3 |
| LP | 142 | 136.7 | −5.3 | 1.02 | 0.41 | 5 |
| RA | 145 | 134.8 | −10.2 | 1.53 | 0.414 | 3 |
| RT | 146 | 144 | −2 | 1.82 | 0.508 | 3 |
| RP | 136 | 143.2 | 7.2 | 1.45 | 0.52 | 0 |
| LA Cage IV | 136 | 146.6 | 10.6 | | 0.473 | 0 |
| LT | 145 | 143.6 | −1.2 | | 0.536 | 3 |
| LP | 135 | 133 | −2 | | 0.48 | 3 |
| RA | 141 | 142.8 | 1.6 | | 0.515 | 2 |
| RT | 133 | 142 | 9 | | 0.558 | 0 |
| RP | 132 | 139.5 | 7.5 | | 0.466 | 3 |
| Combo Mean Score | 139.8333 | 139.8833 | 0.05 | 1.528333 | 0.4735 | 2.583333 |
| Standard Deviation | 5.441145 | 4.440482 | 7.525895 | 0.401667 | 0.055870792 | 1.880925 |
| Standard Error (SD/sqrIN) | 1.570769 | 1.281894 | 2.172602 | 0.164013 | 0.016128982 | 0.542992 |
| P Value By T Test | 0.452759 | 0.026033 | 0.02071 | 0.185971 | 0.097612528 | 0.017137 |

EXAMPLE 2

Effect of SERP-1/Cyclosporin on Inflammation and Heart Failure Associated with Coronary Arterial Occlusion Coronary arterial occlusion with resultant lack of blood flow to the heart, ischemia, and ensuing myocardial damage and necrosis is induced in mongrel dogs by the following procedure. Under sterile conditions, mongrel dogs (28-35 kg) are anaesthetized using intravenous pentobarbital (30-35 mg/kg) and maintained using a continuous infusion of pentobarbital at a rate of approximately 0.05 mg/kg per minute. Succinylcholine (1 mg/kg) is also given intravenously at the time of anaesthesia induction. The animals are then intubated with a cuffed endotracheal tube and ventilated with warm, humidified room air and oxygen through a ventilator such as the Siemens 900 ventilator. A femoral line is inserted and systemic pressure is continuously displayed. Arterial blood samples are drawn periodically to maintain pH, $pO_2$, and $pCO_2$ within physiological limits. Body temperature is maintained at 37° C. with warmed humidified ventilated air and a heat lamp placed over the thorax. Temperature is monitored using a YSI 73A temperature controller (Yellow Springs Instrument Company, Yellow Springs, Ohio) that has a thermistor positioned in the mid-esophagus. Electrocardiographic leads are applied for continuous ECG monitoring. Ten day old and four week old infarcts are created as follows. The heart is exposed under sterile conditions through a limited (4 cm) left thoracotomy at the fourth intercostal space. The pericardium is opened to expose the proximal left anterior descending (LAD) artery and is dissected as proximal to its origin as possible and a nose occluder is applied. Partial occlusion is maintained for thirty minutes and complete occlusion is maintained for ninety minutes. The nose occluder is removed and reperfusion is allowed to occur. A chest tube is inserted and the chest closed in layers. Animals are allowed to recover for four to ten days. In order that an accurate comparison is made between normal and infarcted hearts, control dogs (which are divided into groups that either receive SERP-1/Cyclosporine infusions or are not infused) are subjected to sham LAD occlusion to eliminate possible obfuscating factors secondary to LAD occlusion as well as surgery, thoracotomy, pericardiotomy, adhesions and the like.

After ten days, SERP-1/cyclosporin, at doses ranging from 3 pg/kg to 3 mg/kg, is given by coronary arterial infusion to monitor the effect on inflammation and heart failure in dogs with induced coronary occlusions. Similar doses of SERP-1/cyclosporin are administered by intra-peritoneal (i.p), subcutaneous (s.c.) and intravenous administration (iv).

Dogs are monitored at selected time intervals over a 2-6 month follow up. Echocardiography is used to assess left ventricular function. Routine Hematoxylin and eosin staining of the myocardium is used to monitor the effect of SERP-1/cyclosporin on myocardial inflammation.

EXAMPLE 3

Effect of SERP-1/Cyclosporin on Induced Cardiac Arrhythmias

Dogs with induced arterial occlusions (Example 5) are allowed to recover for six, thirty and sixty days and then subjected to a second surgery for induction of cardiac arrhythmias. After pentobarbital anesthesia similar to that of the first surgery (Example 5), a second surgical procedure is commenced. A midline sternotomy and pericardial cradle is performed with similar hemodynamic monitoring and intravenous infusions as in Example 5. An anodal titanium mesh defibrillation patch electrode (Medtronics TX-7, reduced to 4.5 sq. cm.) is sutured to the right atrium/superior vena cava junction. A cathodal defibrillation patch (Medtronics TX-7, 15 sq. cm.) is sutured to the left ventricular apex. Intervention shocks as well as therapeutic defibrillation shocks are administered by positioning a third titanium mesh defibrillation patch electrode (Medtronics TX-7, reduced to 4.5 sq. cm.) in the area of the RV outflow tract. The aortic root fat pad is dissected free and a 4.0 mm Ag/AgCl reference electrode is sutured to the aortic root to serve as the reference for all DC coupled unipolar recordings. For the initial global epicardial mapping of voltage gradient fields and activations, an epicardial jacket containing uniformly positioned and easily re-positionable tripolar button electrodes is fitted around the heart. After global mapping to confirm the sites of early activation, a greater density of recording electrodes is concentrated over the early activation sites including the infarct and border zones. Previously described transmural and septal recording electrodes may also be used for voltage gradient determinations throughout the heart. After all electrodes are placed, the heart is draped with a 4×4 sponge moistened with warm saline. The sternum is approximated and draped with a plastic sheet and a moist towel to maintain the heart in a moist and constant temperature environment. Ventricular fibrillation is induced by 60 Hz alternating current outside and inside the infarct zone as well as by rapid ventricular pacing in the infarct zone.

SERP-1/cyclosporin at doses ranging from 3 pg/kg to 3 mg/kg, is given by coronary infusion on the day of arterial occlusion surgery or at follow up to monitor the effects on global alteration in the passive properties of conduction as well as lethal ventricular arrhythmias. Time course of change in the passive properties of myocardial conduction in response to administration of SERP-1/Cyclosporine is determined using microscopic endocardial recordings and correlated with deterioration in LV function and the development of ventricular arrhythmias. Wikowski et al., 1993 *Circulation Research* 72:424-439.

EXAMPLE 4

Effect of SERP-1/Cyclosporin on Congestive Heart Failure and Cardiomyopathy

Congestive heart failure and cardiomyopathy is induced in mongrel dogs as follows. Under sterile conditions, mongrel dogs (28-35 kg) are anaesthetized using intravenous pentobarbital (30-35 mg/kg) and maintained using a continuous infusion of pentobarbital at a rate of approximately 0.05 mg/kg per minute. Succinylcholine (1 mg/kg) is also given intravenously at the time of anaesthesia induction. A pace maker is inserted into the right ventricular area of the heart and set on a high rate ranging from 100 to 280 beats per minute. After 14-30 days, SERP-1/Cyclosporine, at doses ranging from 3 pg/kg to 3 mg/kg, is given either by coronary infusion, intra-peritoneal (i.p)., subcutaneous (s.c.) or intravenous administration (iv). Dogs are monitored for effect of SERP-1/cyclosporin on myocardial inflammation and heart failure at selected time intervals over a 2-6 month follow up. Echocardiography is used to assess left ventricular function. Routine hematoxylin and eosin staining of myocardium is used to monitor the effect of SERP-1/Cyclosporin on myocardial inflammation. Immunohistochemical staining of myocardium is used to monitor the effect of SERP-1/Cyclosporine on myocardial infiltration by inflammatory cells. In addition, confocal and electron microscopy studies are performed to monitor differences in spatial distribution and molecular characteristics of gap junctions in SERP-1/Cyclosporin treated myopathic and normal hearts.

EXAMPLE 5

SERP-1/Cyclosporin Treatment of Conditions Associated with Acute Pulmonary Inflammation Sensitization of Animals Sprague-Dailey rats, aged 8-12 weeks are sensitized two weeks before SERP-1/Cyclosporin treatment with 1 mg ovalbumin (OF) grade V and 200 mg $Al(OH)_3$ in 1 ml saline (subcutaneous administration) and 1 ml *Bordetella pertussis* vaccine ($2 \times 10^9$) bacilli (intraperitoneal administration) as adjuvant to potentiate IgE antibody production. Sprague-Dawley rats thus sensitized are used for monitoring the effects of SERP-1 on conditions associated with hyperactive airways such as asthma and bronchitis.

Sprague-Dawley rats infected with the nematode *Nippostrongylus brasiliensis* are used to monitor the effects of SERP-1 on acute allergic reactions specifically related to the pulmonary system such as allergy and hypersensitivity. *N. brasiliensis* sensitized rats, valuable in monitoring allergen-induced pulmonary inflammation, including local neutrophilia, eosinophilia and alveolar macrophage recruitment and function are described in detail in Ramaswamy et al., 1991 *J. Parasitology* 77:302-312 and Mathison et al., 1992 *Br. J. Pharmacology* 106:263-266, incorporated herein by reference.

SERP-1/Cyclosporin Administration and Effects on Acute Pulmonary Inflammation

SERP-1/cyclosporin is administered at selected times after sensitization (*Bordetella pertussis* vaccine or *N. brasiliensis*) by aerosol, subcutaneous, intraperitoneal or intravenous infusions at doses ranging from 3 pg to 3 ug total dose per experimental animal. Sensitized rats are also administered the same volume of saline solution as an experimental control. The effect of SERP-1/cyclosporin treatment is monitored by histology and immunohistochemical analysis of tissue from pulmonary specimens.

In order to monitor effects of SERP-1/cyclosporin on alveolar macrophage functions, sensitized rats and in some cases sensitized rats which have also undergone SERP-1/cyclosporin infusion as described above are exposed to aerosols using the following procedure. Aerosols are generated using the Wright nebulizer from Roxon Medi-Tech Lte (Montreal, PQ) using compressed air with a pressure giving an output of 0.1-0.2 ml/min passed into a plexiglass box. Saline or OA (2% in saline) is nebulized for five minutes to anesthetized rats, thereby delivering Ag in aerosol form.

After exposure to aerosols; SERP-1/cyclosporin is administered via aerosol or subcutaneous, intraperitoneal, or intravenous infusions at doses ranging from 0.3 pg to 3 mg total dose per experimental animal. Aerosol exposed rats are also administered a comparable volume of saline solution as an experimental control. After 0, 6, 10, 30, 60 and 90 days, rats weighing between 190-250 g are anesthetized, the trachea exposed and cannulated with a metal tracheal cannula to which are brazed three other metal tubes. One tube connects to a pressure transducer (such as a Validyne MP45 +/−50 $cmH_2O$) for measuring airway pressure. The other two tubes which form a "Y" allow connection to the inspired and expired pathways of a ventilator such as the Harvard Rodent Ventilator. The ventilator is set to deliver a tidal volume of 8 to 10 ml/kg at a rate of 50-60 breaths per minute.

After the surgical preparation, each tracheotomized rat is placed in a 30×15×10 cm plastic box and the trachea connected to the ventilator and to the airway pressure transducer. The ventilator is started and the box lid closed. Both the airway pressure and the box pressure are directed to a computer and stored in Lotus 1,2,3. Measurements are taken over ten second periods during which the results from 7-10 complete tidal breaths are collected. The box pressure signal represents volume changes due to ventilation and the signal is differentiated to provide inspired and expired flow rate. A spreadsheet is therefore generated which provides data for airway pressure, tidal volume and tidal flow. From this data, respiratory system resistance and dynamic compliance (or elasticity) is calculated, thereby providing a measure of degree of bronchoconstriction for both control (saline infused) and experimental (SERP-1/cyclosporin infused) rats.

Sheep are known to develop both early and late bronchial responses to inhaled *Ascaris suum* antigen and are thus useful in monitoring SERP-1/cyclosporin effects on inflammatory conditions such as asthma and bronchitis. See Abraham et al., 1993 *Am. Rev. Respir. Dis.* 128:839-844 and Abraham et al., 1994 *J. Clin. Invest.* 93:776-787, incorporated herein by reference. After topical anesthesia of the nasal passages, a balloon catheter is advanced through one nostril into the lower esophagus and the animals intubated with a cuffed endotracheal tube. through the other nostril. Pleural pressure is measured with the esophageal balloon catheter filled with about 1 ml air. Lateral pressure in the trachea is measured with a catheter adjacent to the tip of the endotracheal tube and both pleural and tracheal catheters are connected to a differential pressure transducer such as the Validyne MP45, Northridge, Calif. Transpulmonary pressure is determined as the difference between the two pressures. Airflow is measured by connecting the proximal end of the endotracheal tube to a pneumotachograph (Fleis, Dyna Sciences, Inc., Blue Bell Pa.). Pulmonary flow resistance is determined as the temporal change in transpulmonary pressure divided by the change in airflow at mid-tidal volume. Bronchoalveolar lavage is performed using a fiberoptic bronchoscope with aliquots of pH 7.4 buffered saline.

Antigen (typically *Ascaris suum* extract, obtainable from Greer Diagnostics, Lenoir N.C.) is introduced via a conventional medical nebulizer connected to a dosimeter system comprising a solenoid valve, a source of compressed air and a respirator.

Baseline airway response characteristics and bronchoalveolar lavage is performed several days prior to an experimental run. On the day of the experiment, airway responsiveness is again measured and then SERP-1/cyclosporin is introduced via intravenous infusion of about 3 pg/kg to 3 mg/kg or an equivalent volume of saline. After administration of SERP-1/cyclosporin, airway responsiveness (specific lung resistance, mean pulmonary flow resistance and the like) are assayed and the animal is then challenged with antigen. Post challenge determinations of airway responsiveness and post challenge bronchoalveolar lavage are made at various times after antigen challenge. Control and polypeptide trials are separated by at least three weeks, a time interval sufficient for the sheep to recover from past challenges. In another protocol, the effect of administering SERP-1/cyclosporin after antigen challenge is monitored.

In vitro parameters measured to assay the effectiveness of SERP-1/cyclosporin include differential cell counts in the lavage fluid of epithelial cells, macrophages, lymphocytes, neutrophils, basophils, eosinophils and monocytes.

Guinea pigs may also be monitored for the effects of SERP-1 on hyperactive airways such as asthma. See eg., Pretolani et al. 1994 *J. Exp. Med.* 180:795-805. Male Hartley guinea pigs are sensitized by aerosolized albumin (Miles, Naperville, Ill.). The procedure is repeated 48 hours later and the animals are exposed to challenge by ovalbumin aerosol solutions 14-17 days after the first inhalation. Control animals are sensitized as above but are exposed to saline after 14-17 days. SERP-1/cyclosporin is administered to sensitized guinea pigs, about 1 hour before and about 4 hours after antigen challenge.

The effect of SERP-1/cyclosporin administration on antigen-induced bronchial hyperactivity and cellular infiltration is assayed in a number of ways. Changes in bronchial resistance to lung inflation are measured by a pressure transducer placed between the trachea and a respiratory pump and continuously recorded on a dynograph. Bronchial reactivity is tested by repeated administration of methacholine (Sigma Chemical Co.). Alliquots of arterial blood are collected for total leukocyte counts using a Coulter counter and for differential counts after staining. Bronchoalveolar cells are collected in successive lavages using aliquots of sterile saline injected and recovered through a polyethylene tracheal cannula. Differential cell counts and measurement of eosinophil peroxidase is also performed on the lavage fluids. Immunohistochemical studies are performed on dissected lung tissue previously fixed in chloroform-acetone. Sections are stained with a variety of monoclonal antibodies specific for T cells, and activated eosinophils, using conventional techniques such as those described in Pretolani et al. 1994.

EXAMPLE 6

SERP-1/Cyclosporin Treatment of Secondary Immune-Mediated Injury Following Neurotrauma Reproducible injury of the thoracic spinal cord in Lewis rats is induced via an electromechanical impact device as described previously (Stokes et al. 1991 *J. Neurotrauma* 9:187-195; Popovich et al. (1993) *J. Neurotrauma* 10:37-46; Popovich et al. 194 *Brain Research* 633:348-352). Briefly, the electromechanical impact device is used to make brief contusive injuries to the rodent spinal cord (<25 msec total duration). The animals are routinely anesthetized with ketamine (60 mg/kg) and xylazine (10 mg/kg), and a single segment laminectomy is performed at spinal level T8 or T9. The spinal cords are contused with the device by rapid displacement of the spinal cord 1.1 mm from the original cord surface and both displacement and force are recorded continuously. Superficial wounds are then closed in layers and the injured animals allowed to recover.

Injured rats are administered SERP-1/cyclosporin via intravenous routes (0.3 pg to 3 mg dosages) and by intraspinal injections (0.3 pg to 3 mg dosages). Injured rats in a control group are administered a similar volume of saline solution. One, six, fourteen, thirty, sixty and ninety days after SERP-1/cyclosporin infusion, rats are sacrificed by administering sodium phenobarbital (100 mg per kg). The effects of SERP-1/cyclosporin treatment on progressive tissue necrosis following traumatic injury is monitored by histological, biochemical, immunological and behavioral criteria that are known to be associated with neurotrauma in Lewis rats. For example, parenchymal microglia from the central nervous system and infiltrating reactive leukocytes, known to mediate extensive cell death occurring post-trauma are monitored as follows.

Immunohistochemical analysis is performed on formalin fixed sections cut from injured regions of the thoracic spinal cord. Paraffin sections taken from the fixed rabbit spinal cord are immunostained with a variety of standardized cell surface markers such as MHC markers, CD markers for the specific cell subtypes, and the like which measure the extent of microglial activation and levels of leukocyte infiltration into the spinal parenchyma in the area of the contusion lesion produced by the spinal injury device. In addition, assessment of the local expression of standard inflammatory cytokines such as TNF, and IL1 is conducted by RT-PCR and Northern blotting analysis. Lymphocyte activation in the appropriate draining lymphoid tissues are measured by lymphocyte proliferation assays and by the adoptive transfer of spinal injury-activated lymphocytes.

EXAMPLE 7

Effect of SERP-1/Cyclosporin on Inflammatory Bowel Diseases and Psoriasis

Transgenic rats expressing the human class I major histocompatibility allele, HLA-B27, (Hammer et al. 1990 *Cell* 63:1099-1112) are used to monitor the effects of SERP-1/cyclosporin on inflammatory bowel diseases and psoriasis. Virtually all HLA-B27 rats develop chronic gastrointestinal inflammation by age 16 weeks while approximately 70% develop arthritis and a substantial number develop psoriasis during the same time frame. In addition, Cotton top tamarins (CTT) are also used to monitor the effects of SERP-1/cyclosporin on spontaneous and acute colitis resembling ulcerative colitis and Crohn's disease. See Podolsky et al., 1993 *J. Clin. Invest.* 92:372.

SERP-1/cyclosporin is administered to HLA-B27 rats and Cotton-top tamarins by; a variety of routes: intravenous (0.3 pg-3 mg), subcutaneous (0.3 pg-3 mg), intraperitoneal (0.3 pg-3 mg) intra-articular (0.3 pg-3 mg), and intra-rectal (0.3 pg-3 mg). After one to thirty days, tissue samples are collected for analysis of inflammatory parameters. After assessing SERP-1/cyclosporin effects, the number of SERP-1/cyclosporin injections is optimized as needed.

Gut pathology of HLA-B27 mice and Cotton-top tamarins is graded macroscopically and microscopically using established criteria of inflammation. SERP-1/cyclosporin effects on psoriasis are monitored by examining psoriatic lesions and observing changes in scale numbers, epidermal thickening, hyperplasia and staining for the associated inflammatory cells (mostly lymphocytes) in the mouse.

Inflammatory bowel disease in rabbit is induced by colonic administration of trinitrobenzene sulfonic acid (TNBS) as described in Percy et al., 1993 *Gastroenterology* 104:369-376 or chemotactic peptide, f-met-leu-phe as described in LeDuc et al., 1990 *Gastroenterology* 98:929-935. New Zealand white rabbits (3-4 kg) are anesthetized by intramuscular administration of xylazine and ketamine. A Foley catheter is inserted approximately 15 cm into the colon and inflated with 3 ml of air and gently withdrawn to induce muscular clearance of distal fecal matter. A dialysis bag (8-10 cm, n.7, 10 mm diameter, Spectrum Medical Industries, Houston, Tex.) with 3-4 ml of 150 mg/ml TNBS in 50% ethanol is inserted into the distal colon and left in place for one hour. The bag is then removed and animals are treated with intravascular, intraperitoneal, intramuscular, subcutaneous or suppository delivered SERP-1/cyclosporin (3 pg/kg to 3 mg/kg) or saline control. Treatment is either in a single dose immediately following TNBS removal, one hour following TNBS removal, one day following TNBS removal or daily for five days following TNBS removal. Animals are euthanized with pentobarbital (60 mg/kg) 5 days post-TNBS treatment. The distal 5 cm of colon is, analyzed for inflammatory bowel disease. Hematoxylin and eosin stained colon tissue sections are evaluated for the appearance of the lamina propria, submucosa, muscularis mucosae and mucosa with respect to ulceration, crypt abscesses, neutrophil aggregation and the presence of inflammatory infiltrate in the muscularis propria. Colitis is defined as the presence of acute and chronic inflammatory cells in the lamina propria and acute intraepithelial inflammatory cells.

EXAMPLE 8

Effect of SERP-1/Cyclosporin on Psoriasis

The effects of SERP-1/cyclosporin on psoriasis are monitored in mice carrying the flaky skin (fsn) mutation. Psoriatic lesions can also be maintained as skin grafts on normal littermates or nude mice so that the pathologic features of the fsn phenotype can persist independent of the host thymic-derived immune system. Sundberg et al., 1944, *J. Invest. Dermatol.*, 102:781-788.

SERP-1/cyclosporin is administered to fsn/fsn mice or normal littermates or nude mice carrying a skin grafts from fsn/fsn mice by a variety of routes: intravenous (0.3 pg-3 mg), subcutaneous (0.3 pg-3 mg), intraperitoneal (0.3 pg-3 mg) and intra-articular (0.3 pg-3 mg). After 0, 6, 14, 30, 60 and 90 days, tissue samples are collected for analysis of inflammatory parameters. After assessing SERP-1/cyclosporin effects, the number of SERP-1/cyclosporin injections can be increased as needed.

SERP-1/cyclosporin effects on psoriasis are monitored by examining psoriatic lesions and observing changes in scale numbers, epidermal thickening, hyperplasia and staining for the associated inflammatory cells (mostly lymphocytes) in the mouse. Epidermal hyperplasia is measured as an increase in DNA synthesis, estimated by detecting increased $^3$H-thymidine uptake into cells of psoriatic lesions.

The measurement of autoreactive T cell activation by antigen presenting cells from human psoriatic lesions is also used to monitor SERP-1/cyclosporin effects on human psoriatic cell function in vitro. Epidermal cell suspensions are prepared from fresh skin biopsies of normal individuals and individuals suffering from psoriasis. T cells from the same individuals are purified simultaneously, and the epidermal cells containing the antigen presenting cells are co-cultured with autologous, CD4-positive T cells from the same individual to initiate T cell activation. Autoreactive responses are assessed using conventional methods such as, for example, measuring uptake of tritiated thymidine or by quantitation of relative amounts of mRNA for lymphokines such as IL-2, gamma interferon and IL-4.

The ability of SERP-1/cyclosporin to diminish various antigen presenting cells in the lesional (or normal) skin in activating T cells or in activating distinct types of cytokines, is examined by directly adding SERP-1/cyclosporin to the cell/T cell culture. Inhibition of tritiated thymidine uptake within the antigen presenting cell/T cell co-culture indicates SERP-1/cyclosporin inhibition of the autoreactive process. These data are compared with results obtained with buffer and normal skin cell controls.

EXAMPLE 9

Effects of SERP-1/Cyclosporin on Myocarditis

Autoimmune myocarditis is induced in Lewis rats by immunization with cardiac myosin fraction as discussed previously in Kodoma et al., 1994 *Circ. Res.* 75 (2): 278-284.

Immunized rats are randomly assigned to a control or SERP-1/cyclosporin treated group. SERP-1/cyclosporin infusions are administered by a variety of routes: intravenous (3 pg-_3 mg), subcutaneous (3 pg-3 mg), intraperitoneal (3 pg-3 mg) and intra-articular (3 pg-3 mg). Animals are sacrificed and hearts removed for routine histological and immunological analysis. SERP-1/cyclosporin modulating effects on autoimmune myocarditis are monitored by noting reduced size and discoloration in hearts from SERP-1/cyclosporin treated animals on comparison to untreated control animals and noting reduced ratios of heart weight to body weight in hearts from SERP-1/cyclosporin treated animals on comparison to untreated control animals. In addition, SERP-1/cyclosporin ameliorative effects on myocardial muscle loss and replacement fibrosis are also measured by radionuclide assessment and thermodilution dye assessment of cardiac output as well as routine hemodynamic measurements and myocardial weight.

EXAMPLE 10

Effect of SERP-1/Cyclosporin on Insulin Dependent Diabetes

Splenocytes from non-obese diabetic (NOD) mice showing signs of diabetes are harvested and red-cell depleted in parallel with splenocytes from nondiabetic mice as described in Burkly et al., 1994 *Diabetes* 43:529-534. Splenocytes from NOD mice are (a) pre-treated with SERP-1/cyclosporin or (b) pre-treated with nonspecific, isotype-matched immunoglobulin or (c) untreated. Splenocytes are then injected intravenously ($2-3 \times 10^7$ cells in 0.2 ml PBS) into nondiabetic mice. Controls include nondiabetic mice receiving buffered saline or splenocytes from nondiabetic mice.

In an alternative procedure, SERP-1/cyclosporin is administered 0, 6, 14, 30, 60, and 90 days after splenocyte transfer rather than used in pre-treatment of splenocytes from NOD mice. SERP-1/cyclosporin infusions are administered by a variety of routes: intravenous (3 pg-3 mg), subcutaneous (3 pg-3 mg), intraperitoneal (3 pg-3 mg) and intra-articular.(3 pg-3 mg). SERP-1/cyclosporin ameliorative effects on diabetes are monitored by routine assays for urine and plasma glucose levels. Animals are sacrificed and pancreases harvested in 10% formalin PBS for paraffin-embedded sectioning followed by hematoxylin and eosin staining for histology. Islets are scored in a blind experiment and at least 25 islets are examined per individual animal. Degree of insulitis is scored as described in Burkly et al., 1987: grade 0, no insulitis; grade I, peri-insulitis; grade II, the lesion of cell infiltration occupies less than 25% of the islet area; grade III, 25-50% infiltrated and grade IV, more than 50% infiltrated. The percentage of uninfiltrated islets (grade 0), moderately infiltrated islets (grade I-II) and severely infiltrated islets (grade III-IV) is calculated in relation to the total number of islets monitored for each individual animal.

EXAMPLE 11

Effect of SERP-1/Cyclosporin on Stroke

The modulating effect of SERP-1/cyclosporin on central nervous system ischemia is monitored using gerbils, rabbits or rats. Induction of single and repetitive-insult ischemia in gerbils has been described previously in Wishart et al., 1994 *Neuroreport* 5(12): 1541-1544.

Reversible spinal cord ischemia is induced in the rabbit by temporary occlusion of the abdominal aorta. Irreversible cerebral ischemia in rabbits is induced by injection of plastic microspheres (50 microns) into the internal carotid artery so that spheres lodge in the cerebral vasculature. See Bowes et al., 1994 *Stroke* 25 (11);2253-2257.

SERP-1/cyclosporin is administered after initiation of ischemia by either infusion at a dosage range of 3 pg to 3 mg per kg body weight or as an exchange transfusion at a dosage range of 3 pg to 3 mg per kg bodyweight. Effects of SERP-1/cyclosporin are monitored in the animals undergoing reversible ischemia by noting performance differences in a water maze task in SERP-1/cyclosporin treated and control treated animals. SERP-1/cyclosporin effects are monitored in animals undergoing irreversible cerebral ischeemia by measuring the duration of ischemia required to produce permanent paralysis.

Focal ischemia is initiated in rats by occluding a cerebral artery as described in Davis et al., 1994 *Acta. Neurochir. Suppl.* 60:282-284. Prior to initiation of focal ischemia, rats are randomly assigned into an experimental group receiving SERP-1/cyclosporin pretreatment administered subcutaneously, intravenously, intra-arterially, intraperitoneally or into the spinal fluid at dosages of 0.3 pg to 300 ug or a control group receiving saline (or no pretreatment). SERP-1/cyclosporin effects are monitored by histological assessment of infarct volume and analysis of specific gravity as an index of cerebral edema using well known methodologies.

EXAMPLE 12

Effect of SERP-1/Cyclosporin on Multiple Sclerosis

Experimental autoimmune encephalitis (EAE) is an MS-like syndrome-and is induced by injecting experimental animals intraperitoneally with CD-4 positive T cell clones specific for myelin basic protein. Injected T cell clones reactive to myelin basic protein localize in the central nervous system and initiate inflammation. See Ben-Nun et al., 1981 *Eur. J. Immunol.*, 11: 195-199; Hickey et al., 1991 *J. Neurosci. Res.*, 28: 254-260, incorporated herein by reference. Endogenous monocytes and lymphocytes penetrate inflamed vessels in the brain stem and spinal cord.

EAE is induced by injecting about $8 \times 10^6$ cells of the appropriate T cell clone intraperitoneally into Lewis rats. Production and maintenance of the T-cell clone is as described in Ben-Nun et al., 1981 *Eur. J. Immunol.*, 11: 195-199. Rats typically develop hind limb and tail paralysis, within 4-5 days. Yednock et al. 1991 *Nature* 356: 63-66. Briefly, Lewis rats are immunized with myelin basic protein emulsified in saline and complete Freund's adjuvant. After about 9 days, draining lymph nodes are removed, resuspended in supplemented Eagle's medium, and cultured in petri dishes with added myelin basic protein. Lymphoblasts are then separated and concentrated in one step on a Ficoll density gradient. The lymphoblast fraction is recovered, washed and propagated in vitro in Eagle's medium supplemented with concanavalin-A stimulated spleen cells, horse serum, amino acids, pyruvate, 2-mercaptoethanol and antibiotics. T lymphocytes are selected by limiting dilution in microtiter wells containing irradiated syngeneic thymus cells and myelin basic protein. Ben-Nun et al., 1981.

SERP-1/cyclosporin ameliorative effects in M.S. can also be monitored in mouse Hepatitis virus (JHM coronavirus) infected mice. JHM is injected intracerebrally in young mice with subsequent disease progression (Lucas et al. 1979 *Cell* 12:553-560; Robb et al., 1979 *Virology* 94:352-370. SERP-1/cyclosporin is administered prior to, or simultaneously with, administration of the T-cell clone or with JHM strain infection. SERP-1/cyclosporin ameliorative effects on inflammation are monitored using routine hematoxylin and eosin and immunohistochemical staining and an in vitro adhesion assay previously described in Yednock et al. 1991 *Nature* 356:63-66. Sections of 5 day EAE or JHM infected brain are tested for the ability to support leukocyte attachment. Stamper and Woodruff, *J. Exp. Med.*, 144: 828-833, (1976). Leukocytes e.g. human monocytic cells of line U937, at a concentration of about $10^7$ cells $ml^{-1}$ are layered over freshly cut, unfixed 10 um sections of EAE rat brain exposed (experimental) or unexposed (control) to SERP-1/cyclosporin. Attached leukocytes are discerned as more darkly stained than the sectioned brain tissue and located in a different focal plane.

SERP-1/cyclosporin ameliorative effects on cellular infiltration are monitored immunohistochemically using central nervous system sections taken from experimental and control treatments and a variety of available antibodies such as those enumerated in Table 1 of Yednock et al., 1992 *Nature*, 356: 63-66, incorporated herein by reference. The labeled antibody technique is described in Naish S. J., ed. 1989 *Handbook of Immunochemical staining Methods*, Dako Corp., Carpinteria, Calif. For example, experimental and control sections are treated with monoclonal antibody OX-1, (against CD45 which is expressed on all leukocytes) or monoclonal antibody ED1 which recognizes circulating monocytes. Differences in numbers of reactive leukocytes and monocytes between control and experimental sections are noted.

EXAMPLE 13

SERP-1/Cyclosporin Effects on Systemic Lupus Erythematosus (SLE)

NZB/NZW F1 hybrids and MRL (lpr/lpr) mice are two strains of mice which develop spontaneous SLE-like diseases. Female offspring of New Zealand Black/White crosses develop severe immune complex nephritis, anti-DNA antibodies and undergo severe generalized lymphocyte dysfunction within several months after birth and generally die before nine months. See Howie and Helyer 1968 *Adv. Immunol.* 9.:215, incorporated herein.

Similarly, MRL (lpr/lpr) mice develop fatal immune complex glomerulonephritis within six months of birth, accompanied by massive lymphoproliferation with enlarged peripheral lymph nodes and gross splenomegaly. About 10-20% of MRL mice also develop progressive rheumatoid arthritis and vasculitic skin lesions before death. See e.g. Theofilopolous and Dixon, 1985 *Adv. Immunol.* 37:269-390, incorporated herein by reference. Generally, mice younger than about ten weeks are disease free, and mice older than about 16 weeks develop the disease.

Beginning soon after birth, both strains of mice are administered SERP-1/cyclosporin at a dosage of 1 ng to 3 pg/kg-3 mg/kg via intravenous and intraperitoneal routes staggered by time intervals varying from one week to one month. The effect of SERP-1/cyclosporin at ameliorating immune pathology associated with SLE is monitored monthly, using the following standardized criteria: (i) renal function manifested by proteinuria, urea levels in urine, glomerular filtration rates and levels of subcapsular renal hemorrhage; (ii) number of foci of glomerulonephritis in kidney sections; (iii) lymphocyte infiltration of lacrimal and parotid glands; (iv) levels of anti-erythrocyte and anti-DNA and anti-nuclear antibodies; (v) levels of IgM hypergamma globulinaemia; (vi) loss of thymic function, eg. IL-2 production from isolated lymphocytes; (vii) kidney morphology e.g. enlargement of glomerular deposits, (viii) increased plasma TNF/IL-6 and increased concanavalin A-induced and spontaneous cytokine secretion by T-cells.

The aforementioned criteria are measured by assays described in Morrow et al., 1987 *Autoimmune Rheumatic Disease*, Blackwell Scientific Pub., Oxford, incorporated by reference herein. SERP-1/cyclosporin administration is increased to multiple (weekly and monthly) injections as needed.

In an alternative murine model of SLE, mice are injected at birth with semi-allogenic lymphoid cells. Injected mice develop a lupus-like autoimmune syndrome in which donor B cells are polyclonally activated by host alloerotic $CD4^+T$ cells, producing autoantibodies and immune complex mediated glomerulonephritis. See Ramos et al., 1994 *Immunology* 82:287-293, incorporated herein by reference. SERP-1/cyclosporin administration and monitoring of effects are as described above.

EXAMPLE 14

Effect of SERP-1/Cyclosporin on Lund Injury

An animal model of acute lung injury (e.g. ARDS) is described in Doershuk, et al., 1990 *J. Immunol.* 144: 2327-2333. SERP-1/cyclosporin ameliorative effects on lung injury are monitored as follows. First, New Zealand white rabbits weighing 1-4 kg are anesthetized with ketamine (25-40 mg/kg i.v.) and acepromazine maleate (2-3 mg/kg). Following tracheotomy, a narrow flexible tube is inserted and passed into the peripheral bronchus using fluoroscopy. Rabbits are treated with intravascular, intraperitoneal, subcutaneous, inhaled aerosolized SERP-1/cyclosporin at doses of 3 pg to 3 mg/kg (or saline control) 20 minutes prior to or 20 minutes following instillation of inflammatory stimuli. Pulmonary inflammation is induced by intrabronchial infusion of one of three types of stimuli: *S. pneumonia* (0.15 ml/kg, $10^9$ organisms/ml saline with 7% colloidal carbon), hydrochloric acid (0.15 ml/kg, 10 ug/ml saline with 10% monsteral blue), or phorbol myristate acetate (25 ug/kg with 10% monasteral blue). The tube is then removed and the incision sutured. Pulmonary inflammation is monitored at 20 minutes, 1, 2, 4, 6, and 12 hours post inflammatory stimulus instillation by removal of the lung, preparation of tissue sections stained with eosin/hematoxylin and morphometric quantitation of PMN or PMN versus red blood cell (RBC) infiltration in alveoli. Catheters are removed during anesthesia (5-10 mg/kg ketamine with local 1% lidocaine). Animals are maintained under standard conditions in cages and are monitored daily for weight, Hct and arterial blood gases. At five days post-hemorrhage, the animals are euthanized by pentobarbital overdose and necropsy performed. Organs are examined for gross evidence of injury in tissue sections stained with hematoxylin and eosin. Lungs are analyzed histologically and bronchial alveolar lavage fluid is analyzed for cell counts and leukocyte infiltration.

Animal models of septic and endotoxic shock are described in Harlan et al. 1992 *J. Applied Physiol.* 73(4): 1510-1516. Using these models, 3 pg to 300 ug doses of SERP-1/cyclosporin are administered to animals prior to and/or following endotoxin infusion or appendectomy daily for three days via intravascular, intramuscular, subcutaneous, inhaled aerosol or intraperitoneal administration. SERP-1/cyclosporin efficacy in preventing shock is monitored in sacrificed animals from days 1 through 5 following endotoxin infusion or appendectomy using the above described methods.

An additional model of lung injury due to endotoxic shock in rats is described in Rabinovici et al., 1992 *J. Immunol.* 149:1744-1750 and SERP-1/cyclosporin administration and analysis of lung and organ injury is performed in this model as described above.

EXAMPLE 15

Effect of SERP-1/Cyclosiorin on Ischemia and Reperfusion Injury

Two models of local ischemia/reperfusion injury are described in Mihelcic et al, 1994 *Blood* 84:2322-2328 and Kelly et al, 1994 *Proc. Natl. Acad. Sci* 91:812-816. A local and remote ischemia/reperfusion injury model is described in Hill et al., 1992 *J. of Immunol.* 149:1723-1728.

New Zealand white rabbits (1.5 to 3 kg) are anesthetized with intravenous ketamine and xylazine. A peripheral ear vein is cannulated and a local nerve bloc accomplished by injection of lidocaine at the base of the ear. This ear is then transected at its base leaving intact only the central artery, central vein and a small portion of supporting cartilage. All nerves to the distal segment of the ear are cut, rendering the ear completely anesthetic. A microvascular clip is placed on the central artery of the left ear to produce complete ischemia. The ear is then reattached with suture and the microvascular clip allowed to exit through the wound. The ear is reperfused by removal of the clip after six hours. At the time of reperfusion, a bolus injection of SERP-1/cyclosporin at dosages of 3 pg/kg to 3 mg/kg is given either intravenous, intraperitoneal, subcutaneous or intramuscular. Ambient temperature between 23.5° C. and 24° C. is maintained throughout the procedure.

Injury manifested by edema is determined by submerging the ear into a beaker of water up to the suture line and measuring displacement. Tissue necrosis is determined as percentage necrotic area compared to total surface area. These measurements are performed by an unbiased observer. Neutrophil infiltration is measured using the myeloperoxidase assay using a tissue extract from the rabbit ear.

Male Sprague-Dawley rats weighing 1.6-1.9 kg are fasted for 12 hours prior to surgery. After sodium pentobarbital (65 mg/kg) and 6 ml 0.9% NaCl are administered for anesthesia, the renal artery and vein are surgically exposed and occluded bilaterally for 30 minutes with microaneurysm clamps. SERP-1/cyclosporin is administered in doses of 3 pg/kg to 3 mg/kg by intravenous, intraperitoneal, subcutaneous, or intramuscular injection upon release of the clamped renal vessels. At time points ranging from 0 to 72 hours post-reperfusion, tail vein blood samples are taken and analyzed for urea nitrogen (BUN), a standard urease assay/conductivity assay and creatinine using picric acid reactions. For histochemical analysis of injury, rats are sacrificed at time points from 0.5 to 72 hours and kidney tissue is fixed in formalin, sectioned and stained with hematoxylin and eosin. The percent of tubules in the outer medulla showing epithelial necrosis or necrotic debris is quantitated by blinded observers. Myeloperoxidase assays are performed on kidney tissue collected at time points ranging from 0.5 to 72 hours post-reperfusion to measure neutrophil infiltration.

EXAMPLE 16

Effect of SERP-1/Cyclosporin on Renal Failure

Glomerulonephritis is induced by anti-glomerular basement membrane antibody in rat. WKY rats (300-350 kg) are anesthetized by intraperitoneal injection of ketamine (25-30 mg/kg) and sodium pentobarbital (50 mg/kg). SERP-1/cyclosporin in doses from 3 pg/kg to 3 mg/kg is administered either by intravascular, intramuscular, intraperitoneal or subcutaneous injection. Sheep anti-rat glomerular basement membrane IgG or control IgG (0-10 mg) is intravenously administered. Rats are then housed in metabolic cages for 24 hour intervals for up to 10 days following anti-GBM to measure proteinuria. Total urinary protein is measured using standard Lowry assays. Some animals receive in addition to the initial administration of SERP-1/cyclosporin, daily doses of SERP-1/cyclosporin from 3 pg/kg to 3 mg/kg administered by intravascular, intramuscular, intraperitoneal or subcutaneous injection. Animals are sacrificed at various times and the kidneys removed, fixed, and sectioned. Hematoxylin and eosin stained or toluidine blue stained sections of renal tissue are analyzed for inflammatory cell infiltration, crescent formation, hypercellularity and sclerotic tissue. Extracellular matrix formations detected by staining with anti-fibronectin and anti-tenascin antibodies.

Another model of rat glomerular sclerosis in Sprague-Dawley rats using anti-thymocyte serum is described in detail in Okuda et al., 1990 *J. Clin. Invest.* 86:453-462. Using this model, SERP-1/cyclosporin is administered in doses from 3 pg/kg to 3 mg/kg by intravascular, intramuscular, intraperitoneal or subcutaneous injection on a daily basis following serum infusion for up to 7 days. Histological sections of renal tissue from 0 to 7 days post-serum infusion are stained with hematoxylin and eosin or anti-tenascin antibodies to determine gross injury, inflammatory cell infiltration and sclerosis.

EXAMPLE 17

Effect of SERP-1 on Systemic Shock

New Zealand white rabbits weighing 1-1.5 kg are anesthetized with ketamine (30 mg/kg i.v.). Under sterile conditions, central venous and thermistor-tipped aortic catheters (et. model 94-011, American Edwards Laboratories, Santa Ana, Calif.) are placed through an open femoral approach with local 1% lidocaine supplement. Arterial blood pressure (BP), central venous pressure and core temperature are monitored continuously. Periodic determinations are made of arterial blood gases, hematocrit (Hct), white blood cell count (WBC), and relative thermodilution cardiac output (CO) using a cardiac output/lung water computer (American Edwards Laboratories). After recovery from anesthesia, each animal is treated with intravenous, intramuscular, subcutaneous or intraperitoneal SERP-1 from 3 pg/kg to 3 mg/kg doses or saline control 30 minutes prior to and/or following hemorrhage. Hemorrhagic shock is accomplished by withdrawal of blood via the venous catheter into a heparinized (10 u/ml) polypropylene syringe to maintain a mean BP of 45 tott and mean CO of 30% baseline for one hour. Animals are then resuscitated with the entire volume of shed blood plus lactated Ringer's titrated to restore normal CO. This resuscitation is continued for three hours at which time the catheters are removed during anesthesia (5-10 mg/kg ketamine with local 1% lidocaine).

Animals maintained under standard conditions in cages and are monitored daily for weight, Hct and arterial blood gases. At 5 days post-hemorrhage, the animals are euthanized by pentobarbital overdose and necropsy performed. Organs are examined for gross evidence of injury and histological evidence of injury in tissue sections stained with hematoxylin and eosin.

Animal models of septic and endotoxic shock are described in Thomas et al., 1992 *J. Applied Physiol.* 73(4): 1510-1516. Using these models, 3 pg/kg to 3 mg/kg doses of SERP-1/cyclosporin are administered to animals prior to and/or following endotoxin infusion or appendectomy daily for three days via intravenous, intramuscular, subcutaneous or intraperitoneal administration. SERP-1/cyclosporin efficacy in preventing shock is monitored in sacrificed animals from days 1 through 5 following endotoxin infusion or appendectomy.

What is claimed is:

1. A method of treating arthritis in diseased tissues of a mammalian subject corn pris ing administering to said subject a therapeutically effective amount of SERP-1, SERP-1 analog, or biologically active fragment thereof, and an immunosuppressant, wherein said SERP-1, SERP-1 analog, or biologically active fragment thereof acts synergistically with said immnunosuppressant to improve arthritic clinical score.

2. The method of claim 1 comprising administering to said subject a therapeutically effective amount of SERP-1.

3. The method claim 2, wherein said SERP-1 comprises the sequence of SEQ ID NO: 1.

4. The method of claim 2, wherein said SERP-1 comprises an amino acid sequence comprising the sequence set forth in SEQ ID NO: 1 with a substitution of any amino acid other than cysteine at position 244 of SEQ ID NO: 1.

5. The method of claim 1 comprising administering to said subject a therapeutically effective amount of biologically active fragment of SERP-1.

6. The method of any one of claims 2, 3, or 5, wherein said immunosuppressant is cyclosporin A or PK506.

7. The method of any one of claims 2, 3, or 5, wherein said mammalian subject is human.

8. The method of any one of claims 2, 3, or 5, wherein said arthritis is rheumatoid arthritis.

9. The method of any one of claims 2, 3, or 5, wherein said immunosuppressant is administered prior to administration of a therapeutically effective amount of said SERP-1 or said biologically active fragment or SERP-1.

10. The method of any one of claims 2, 3, or 5, wherein said SERP-1 or said biologically active fragment of SERP-1 is delivered by intravenous, intra-arterial, intra-articular, subcutaneous, intraperitoneal, intraspinal, intrarectal, intramuscular infusion, or aerosol inhalant.

* * * * *

UNITED STATES PATENT AND TRADEMARK OFFICE
CERTIFICATE OF CORRECTION

PATENT NO. : 7,419,670 B2  Page 1 of 1
APPLICATION NO. : 10/381875
DATED : September 2, 2008
INVENTOR(S) : Zhong et al.

It is certified that error appears in the above-identified patent and that said Letters Patent is hereby corrected as shown below:

Title Page, Item (56), Under References Cited, U.S. Patent Documents, in 5,917,014 A, replace "McFaddenm" with --McFadden--.

Column 2, Line 51, replace "mellitis" with --mellitus--;

Line 56, replace "calls" with --cells--; and

Line 57, replace "microabcesses" with --microabscesses--.

Column 3, Line 25, replace "leporipoxyiral" with --leporipoxyviral--.

Column 6, Line 28, replace "microabcesses" with --microabscesses--.

Column 20, Line 1, replace "Alliquots" with --Aliquots--.

Column 31, Line 12, replace "corn pris ing" with --comprising--; and

Line 17, replace "immnunosuppressant" with --immunosuppressant--.

Signed and Sealed this

Fifth Day of October, 2010

David J. Kappos
*Director of the United States Patent and Trademark Office*